US012644805B2

(12) United States Patent
Defreitas et al.

(10) Patent No.: US 12,644,805 B2
(45) Date of Patent: Jun. 2, 2026

(54) APPARATUS AND ASSOCIATED METHODS FOR REDUCING FLUID IN BIOPSY TISSUE HANDLING SYSTEM FOR IMPROVING IMAGING QUALITY

(71) Applicant: HOLOGIC, INC., Marlborough, MA (US)

(72) Inventors: Kenneth F. Defreitas, Patterson, NY (US); Tim Stango, Marlborough, MA (US); Tom Farbizio, Patterson, NY (US)

(73) Assignee: Hologic, Inc., Marlborough, MA (US)

( * ) Notice: Subject to any disclaimer, the term of this patent is extended or adjusted under 35 U.S.C. 154(b) by 1029 days.

(21) Appl. No.: 17/779,891

(22) PCT Filed: Nov. 25, 2020

(86) PCT No.: PCT/US2020/062181
§ 371 (c)(1),
(2) Date: May 25, 2022

(87) PCT Pub. No.: WO2021/108515
PCT Pub. Date: Jun. 3, 2021

(65) Prior Publication Data
US 2023/0014922 A1 Jan. 19, 2023

Related U.S. Application Data

(60) Provisional application No. 62/941,395, filed on Nov. 27, 2019.

(51) Int. Cl.
*G01N 1/40* (2006.01)
*A61B 10/00* (2006.01)
(52) U.S. Cl.
CPC ........... *G01N 1/40* (2013.01); *A61B 10/0096* (2013.01)

(58) Field of Classification Search
CPC .............................. G01N 1/40; A61B 10/0096
See application file for complete search history.

(56) References Cited

U.S. PATENT DOCUMENTS

| | | | |
|---|---|---|---|
| 4,038,988 | A | 8/1977 | Perisse |
| 4,134,012 | A | 1/1979 | Smallbone et al. |
| | | (Continued) | |

FOREIGN PATENT DOCUMENTS

| | | |
|---|---|---|
| CN | 104583754 A | 4/2015 |
| CN | 204489169 U | 7/2015 |
| | (Continued) | |

OTHER PUBLICATIONS

International Search Report and Written Opinion of the International Searching Authority for International Patent Application No. PCT/US2020/062181 mailed May 5, 2021, 15 pages.
(Continued)

*Primary Examiner* — Samuel P Siefke
(74) *Attorney, Agent, or Firm* — Merchant & Gould P.C.

(57) ABSTRACT

A tissue holder assembly includes: a base comprising a bottom member, a central hub extending upwardly from the bottom member, and a circumferential sidewall extending upwardly from the bottom member radially spaced apart from the hub, the circumferential sidewall surrounding the hub and defining an interior region configured for accommodating a cylindrical tissue holder; the base further comprising a raised platform spaced upwardly apart from the bottom member, the central hub extending through a central opening of the platform and configured for supporting the tissue holder; the bottom member, the hub, and the circumferential sidewall collectively defining an annular fluid channel underlying the platform; wherein the fluid channel extends around the hub from an opening in the platform to a fluid exit port in the circumferential sidewall; the base
(Continued)

further comprising a flow comb underlying the platform opening and extending into the fluid channel.

19 Claims, 12 Drawing Sheets

(56)                    References Cited

U.S. PATENT DOCUMENTS

| | | | |
|---|---|---|---|
| 4,306,570 A | 12/1981 | Matthews | |
| 4,549,554 A | 10/1985 | Markham | |
| 4,658,834 A | 4/1987 | Blankenship et al. | |
| 4,802,195 A | 1/1989 | Wojciechowski | |
| 4,803,639 A | 2/1989 | Steele | |
| 4,837,795 A | 6/1989 | Garrigus | |
| 4,852,560 A | 8/1989 | Hermann, Jr. | |
| 5,023,894 A | 6/1991 | Yamashita | |
| 5,023,895 A | 6/1991 | McCroskey | |
| 5,256,160 A | 10/1993 | Clement | |
| 5,427,742 A | 6/1995 | Holland | |
| 5,456,689 A | 10/1995 | Kresch et al. | |
| 5,491,344 A | 2/1996 | Kenny et al. | |
| 5,505,210 A | 4/1996 | Clement | |
| 5,526,822 A | 6/1996 | Burbank et al. | |
| 5,541,856 A | 7/1996 | Hammermeister | |
| 5,575,293 A | 11/1996 | Miller et al. | |
| 5,609,827 A | 3/1997 | Russell | |
| 5,754,621 A | 5/1998 | Suzuki | |
| 5,983,125 A | 11/1999 | Alfano et al. | |
| 6,017,316 A | 1/2000 | Ritchart et al. | |
| 6,032,673 A | 3/2000 | Savage et al. | |
| 6,058,159 A | 5/2000 | Conway | |
| 6,163,590 A | 12/2000 | Wilkins | |
| 6,207,111 B1 | 3/2001 | Weinberg | |
| 6,225,107 B1 | 5/2001 | Nagle | |
| 6,234,672 B1 | 5/2001 | Tomasetti et al. | |
| 6,322,522 B1 | 11/2001 | Zimmon | |
| 6,403,035 B1 | 6/2002 | Caratsch et al. | |
| 6,485,436 B1 | 11/2002 | Truckai et al. | |
| 6,535,284 B1 | 3/2003 | Hajduk et al. | |
| 6,646,721 B2 | 11/2003 | Compter | |
| 6,899,850 B2 | 5/2005 | Haywood | |
| 7,166,113 B2 | 1/2007 | Arambula | |
| 7,175,612 B2 | 2/2007 | Felix et al. | |
| 7,397,894 B2 | 7/2008 | Nakai | |
| 7,546,925 B1 | 6/2009 | Zuk, Jr. | |
| 7,616,801 B2 | 11/2009 | Gkanatsios et al. | |
| 7,662,109 B2 | 2/2010 | Hibner | |
| 7,692,144 B2 | 4/2010 | Watanabe | |
| 7,715,523 B2 | 5/2010 | Lafferty | |
| 7,753,857 B2 | 7/2010 | Hibner | |
| 7,758,601 B2 | 7/2010 | Heywang-Koebrunner et al. | |
| 7,826,588 B2 | 11/2010 | Eliasson | |
| 7,854,705 B2 | 12/2010 | Pawluczyk et al. | |
| 7,856,081 B2 | 12/2010 | Peschmann | |
| 7,858,038 B2 | 12/2010 | Andreyko et al. | |
| 7,867,173 B2 | 1/2011 | Hibner et al. | |
| 7,869,563 B2 | 1/2011 | DeFreitas et al. | |
| 7,881,427 B2 | 2/2011 | Kalender et al. | |
| 7,881,428 B2 | 2/2011 | Jing et al. | |
| 7,972,062 B2 | 7/2011 | Nicolosi | |
| 8,038,347 B2 | 10/2011 | Manak | |
| 8,038,627 B2 | 10/2011 | Hibner | |
| 8,050,735 B2 | 11/2011 | Feke | |
| 8,052,616 B2 | 11/2011 | Andrisek et al. | |
| 8,162,140 B2 | 4/2012 | Hansen | |
| 8,177,728 B2 | 5/2012 | Hibner et al. | |
| 8,213,570 B2 | 7/2012 | Panesar | |
| 8,217,357 B2 | 7/2012 | Stein et al. | |
| 8,235,913 B2 | 8/2012 | Hibner et al. | |
| 8,284,896 B2 | 10/2012 | Singh | |
| 8,532,745 B2 | 9/2013 | DeFreitas et al. | |
| 8,565,374 B2 | 10/2013 | DeFreitas et al. | |
| 8,702,623 B2 | 4/2014 | Parihar | |
| 8,741,232 B2 | 6/2014 | Baysal | |
| 8,764,679 B2 | 7/2014 | Miller et al. | |
| 8,787,522 B2 | 7/2014 | Smith et al. | |
| 8,838,207 B2 | 9/2014 | Nakayama et al. | |
| 8,873,716 B2 | 10/2014 | Ren et al. | |
| 8,911,381 B2 | 12/2014 | Hibner et al. | |
| 8,923,603 B2 | 12/2014 | Weston | |
| 8,956,306 B2 | 2/2015 | Hibner | |
| 8,971,484 B2 | 3/2015 | Beckmann | |
| 8,983,030 B2 | 3/2015 | Ookawa | |
| 9,020,579 B2 | 4/2015 | Smith et al. | |
| 9,066,706 B2 | 6/2015 | DeFreitas et al. | |
| 9,068,920 B2 | 6/2015 | Churilla | |
| 9,129,715 B2 | 9/2015 | Adler | |
| 9,188,696 B2 | 11/2015 | Schafer | |
| 9,234,855 B2 | 1/2016 | Watanabe | |
| 9,277,895 B2 | 3/2016 | Hara | |
| 9,322,790 B2 | 4/2016 | Ookawa | |
| 9,326,755 B2 | 5/2016 | Fiebig | |
| 9,329,139 B2 | 5/2016 | Itou | |
| 9,341,546 B2 | 5/2016 | Stuke | |
| 9,347,894 B2 | 5/2016 | Sims | |
| 9,492,130 B2 * | 11/2016 | Flagle ................. A61B 6/4405 |
| 9,498,175 B2 | 11/2016 | Stein et al. | |
| 9,549,709 B2 | 1/2017 | DeFreitas et al. | |
| 9,642,581 B2 | 5/2017 | Lowe | |
| 9,668,711 B2 | 6/2017 | Smith et al. | |
| 9,733,167 B2 | 8/2017 | Wismueller | |
| 9,750,484 B2 | 9/2017 | Finke et al. | |
| 9,861,327 B2 | 1/2018 | Yasuda et al. | |
| 9,865,424 B2 | 1/2018 | Ikeda | |
| 9,901,320 B2 | 2/2018 | DeFreitas et al. | |
| 9,943,850 B2 | 4/2018 | Purdy | |
| 9,953,799 B2 | 4/2018 | Hakoda | |
| 10,008,298 B2 | 6/2018 | King | |
| 10,010,296 B2 | 7/2018 | Basu | |
| 10,078,093 B2 | 9/2018 | Flagle | |
| 10,098,216 B2 | 10/2018 | Kabumoto | |
| 10,105,709 B2 | 10/2018 | Purdy | |
| 10,145,806 B2 | 12/2018 | Tanaka | |
| 10,190,997 B2 | 1/2019 | Aoki | |
| 10,194,875 B2 | 2/2019 | DeFreitas et al. | |
| 10,201,331 B2 | 2/2019 | Fleming | |
| 10,322,412 B2 | 6/2019 | Purdy | |
| 10,393,678 B2 | 8/2019 | Watanabe | |
| 10,488,351 B2 | 11/2019 | Butani | |
| 10,489,964 B2 | 11/2019 | Wang | |
| 10,542,951 B2 | 1/2020 | Klausz et al. | |
| 10,561,387 B2 | 2/2020 | Smith et al. | |
| 10,631,809 B2 | 4/2020 | Noh | |
| 10,705,030 B2 | 7/2020 | Watanabe | |
| 10,709,396 B2 | 7/2020 | Lou | |
| 10,729,403 B2 | 8/2020 | DeFreitas et al. | |
| 10,753,836 B2 | 8/2020 | O'Driscoll | |
| 10,792,003 B2 | 10/2020 | Smith et al. | |
| 10,809,208 B2 | 10/2020 | Yashima | |
| 10,827,989 B2 | 11/2020 | Vancamberg et al. | |
| 10,905,385 B2 | 2/2021 | DeFreitas et al. | |
| 11,083,426 B2 | 8/2021 | DeFreitas | |
| 11,191,502 B2 | 12/2021 | Smith et al. | |
| 11,246,551 B2 | 2/2022 | Butani | |
| 11,478,206 B2 | 10/2022 | Smith et al. | |
| 11,617,548 B2 | 4/2023 | DeFreitas et al. | |
| 2002/0007188 A1 | 1/2002 | Arambula | |
| 2002/0145722 A1 | 10/2002 | Compter | |
| 2002/0193656 A1 | 12/2002 | Ravins et al. | |
| 2003/0087423 A1 | 5/2003 | Haywood | |
| 2003/0216730 A1 | 11/2003 | Barry et al. | |
| 2004/0022350 A1 | 2/2004 | Gregerson et al. | |
| 2004/0174031 A1 | 9/2004 | Rasmussen | |
| 2004/0218716 A1 | 11/2004 | Freifeld | |
| 2005/0051723 A1 | 3/2005 | Neagle et al. | |
| 2005/0065453 A1 | 3/2005 | Shabaz et al. | |
| 2005/0112034 A1 | 5/2005 | McCormick | |
| 2005/0124913 A1 | 6/2005 | Damarati | |
| 2005/0148842 A1 | 7/2005 | Wang | |
| 2006/0074343 A1 | 4/2006 | Hibner | |
| 2006/0116603 A1 | 6/2006 | Shibazaki et al. | |
| 2006/0173266 A1 | 8/2006 | Pawluczyk et al. | |
| 2007/0106176 A1 | 5/2007 | Mark et al. | |
| 2007/0116612 A1 | 5/2007 | Williamson | |

(56) References Cited

U.S. PATENT DOCUMENTS

| | | |
|---|---|---|
| 2007/0166834 A1 | 7/2007 | Williamson, IV et al. |
| 2007/0237684 A1 | 10/2007 | Hansen |
| 2007/0239067 A1 | 10/2007 | Hibner et al. |
| 2007/0270714 A1 | 11/2007 | Cushner et al. |
| 2008/0004545 A1 | 1/2008 | Garrison |
| 2008/0082021 A1* | 4/2008 | Ichikawa ........... A61B 10/0096 600/104 |
| 2008/0132805 A1 | 6/2008 | Heywang-Koebrunner et al. |
| 2008/0137935 A1 | 6/2008 | Spahn |
| 2008/0214955 A1 | 9/2008 | Speeg et al. |
| 2008/0221480 A1 | 9/2008 | Hibner et al. |
| 2008/0228103 A1 | 9/2008 | Ritchie et al. |
| 2008/0249434 A1 | 10/2008 | Hashimshony et al. |
| 2009/0088663 A1 | 4/2009 | Miller et al. |
| 2009/0088666 A1 | 4/2009 | Miller et al. |
| 2009/0131818 A1 | 5/2009 | Speeg et al. |
| 2009/0131820 A1 | 5/2009 | Speeg |
| 2009/0131823 A1 | 5/2009 | Andreyko et al. |
| 2009/0171243 A1 | 7/2009 | Hibner et al. |
| 2009/0171244 A1 | 7/2009 | Ning |
| 2009/0213987 A1 | 8/2009 | Stein |
| 2010/0080346 A1 | 4/2010 | Kalender et al. |
| 2010/0081964 A1 | 4/2010 | Mark |
| 2010/0152611 A1 | 6/2010 | Parihar |
| 2010/0160824 A1 | 6/2010 | Parihar |
| 2010/0160826 A1 | 6/2010 | Parihar |
| 2010/0191145 A1 | 7/2010 | Lafferty |
| 2010/0317997 A1 | 12/2010 | Hibner |
| 2011/0123074 A1 | 5/2011 | Nie |
| 2011/0142201 A1 | 6/2011 | Eberhard et al. |
| 2011/0285837 A1 | 11/2011 | Bello |
| 2012/0014504 A1 | 1/2012 | Jang et al. |
| 2012/0051514 A1 | 3/2012 | Sims et al. |
| 2012/0053484 A1 | 3/2012 | Parks |
| 2012/0065542 A1 | 3/2012 | Hibner et al. |
| 2012/0116246 A1 | 5/2012 | Hibner |
| 2012/0123295 A1 | 5/2012 | Sanbuichi |
| 2012/0245485 A1 | 9/2012 | Hibner |
| 2013/0053724 A1 | 2/2013 | Fiebig |
| 2013/0101089 A1 | 4/2013 | Cho |
| 2013/0231585 A1 | 9/2013 | Flagle |
| 2014/0039343 A1 | 2/2014 | Mescher |
| 2014/0051986 A1 | 2/2014 | Zhao et al. |
| 2014/0065656 A1 | 3/2014 | Baysal |
| 2014/0072104 A1 | 3/2014 | Jacobsen et al. |
| 2014/0198893 A1 | 7/2014 | Badawi et al. |
| 2014/0257135 A1 | 9/2014 | DeFreitas |
| 2014/0276209 A1 | 9/2014 | Hibner |
| 2015/0083893 A1 | 3/2015 | Wismueller |
| 2015/0131773 A1 | 5/2015 | Lowe et al. |
| 2015/0209017 A1 | 7/2015 | Fleming |
| 2016/0073988 A1 | 3/2016 | Nagai |
| 2016/0151054 A1 | 6/2016 | An |
| 2016/0211045 A1 | 7/2016 | Jeon et al. |
| 2017/0131311 A1 | 5/2017 | Flagle |
| 2017/0309063 A1 | 10/2017 | Wang |
| 2017/0336706 A1 | 11/2017 | Wang |
| 2018/0168523 A1 | 6/2018 | Vancamberg et al. |
| 2018/0249985 A1 | 9/2018 | DeFreitas et al. |
| 2019/0054217 A1 | 2/2019 | Axon |
| 2019/0072463 A1 | 3/2019 | O'Driscoll |
| 2019/0130563 A1 | 5/2019 | Vecchio et al. |
| 2019/0167869 A1 | 6/2019 | Willard et al. |
| 2019/0195754 A1 | 6/2019 | Keller |
| 2019/0269376 A1 | 9/2019 | Butani |
| 2019/0285558 A1 | 9/2019 | DeFreitas |
| 2019/0346471 A1 | 11/2019 | Flagle |
| 2020/0029927 A1 | 1/2020 | Wilson et al. |
| 2020/0061622 A1 | 2/2020 | Purdy |
| 2020/0085393 A1 | 3/2020 | Zhang et al. |
| 2020/0160522 A1 | 5/2020 | Merlo |
| 2020/0187923 A1 | 6/2020 | Safir |
| 2020/0268331 A1 | 8/2020 | Purdy |
| 2020/0352543 A1 | 11/2020 | DeFreitas et al. |
| 2020/0386657 A1 | 12/2020 | O'Driscoll |
| 2022/0015729 A1 | 1/2022 | Purdy et al. |
| 2022/0015731 A1 | 1/2022 | Liu |
| 2022/0110597 A1 | 4/2022 | Chen |
| 2022/0133252 A1 | 5/2022 | Smith et al. |
| 2022/0331808 A1 | 10/2022 | Purdy |
| 2023/0012310 A1 | 1/2023 | Stango |
| 2023/0121010 A1 | 4/2023 | Smith et al. |
| 2023/0172572 A1 | 6/2023 | Bumdra |
| 2023/0355200 A1 | 11/2023 | Ren |
| 2024/0016461 A1 | 1/2024 | Wolff |
| 2024/0219276 A1 | 7/2024 | DeFreitas |
| 2024/0315676 A1 | 9/2024 | Chen |
| 2024/0359187 A1 | 10/2024 | Purdy |
| 2025/0166798 A1 | 5/2025 | Tripathi |

FOREIGN PATENT DOCUMENTS

| | | |
|---|---|---|
| CN | 110023994 A | 7/2019 |
| CN | 110393553 A | 11/2019 |
| DE | 20 2019 106 995 | 1/2020 |
| EP | 2277445 | 1/2011 |
| EP | 2007287 | 6/2016 |
| EP | 3143937 | 3/2017 |
| GB | 2018601 | 10/1979 |
| JP | 2006-346179 | 12/2006 |
| JP | 2014-526937 | 10/2014 |
| JP | 2015-085056 | 5/2015 |
| JP | 2015-520402 | 7/2015 |
| JP | 2016-154878 | 9/2016 |
| JP | 2017099928 | 6/2017 |
| JP | 6320717 B2 | 5/2018 |
| WO | 8101363 | 5/1981 |
| WO | 2007021905 | 2/2007 |
| WO | 2008/025146 | 3/2008 |
| WO | 2009/120206 | 10/2009 |
| WO | 2010/028208 | 3/2010 |
| WO | 2011/140374 | 11/2011 |
| WO | 2012/074885 | 6/2012 |
| WO | 2013/166497 | 11/2013 |
| WO | 2017/060726 | 4/2017 |
| WO | 2018/183086 | 10/2018 |
| WO | 2018/204710 A1 | 11/2018 |
| WO | 2019/051496 | 3/2019 |
| WO | 2019/085342 | 5/2019 |
| WO | 2019/216766 | 11/2019 |
| WO | 2020/106888 | 5/2020 |
| WO | 2021/202455 | 10/2021 |

OTHER PUBLICATIONS

PCT International Preliminary Report on Patentability in Application PCT/US2020/062181, mailed Jun. 9, 2022, 12 pages.

Watanabe, M. et al., "The quantitative analysis of thin specimens: a review of progress from the Cliff-Lorimer to the new zeta-factor methods", Journal of Microscopy, vol. 221, No. 2, Feb. 1, 2006, p. 91.

European Extended Search Report in Application 23186924.9, mailed Oct. 23, 2023, 8 pages.

Basak Erguvan-Dogan et al., "Specimen Radiography in Confirmation of MRI-Guided Needle Localization and Surgical Excision of Breast Lesions", American Journal of Roentgenology, American Roentgen Ray Society, vol. 187, No. 2: 339-344 (2006).

* cited by examiner

100

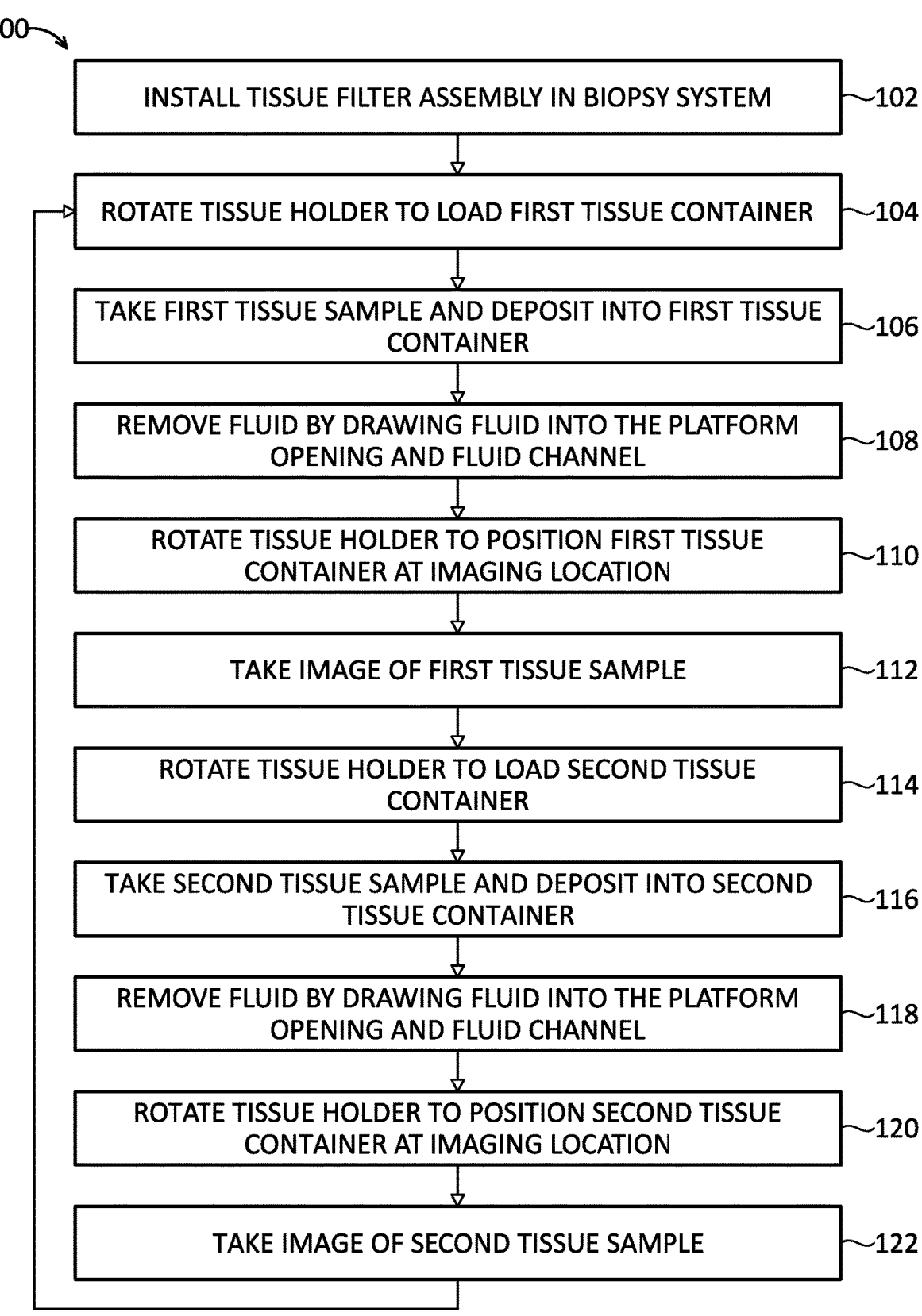

INSTALL TISSUE FILTER ASSEMBLY IN BIOPSY SYSTEM ~102

ROTATE TISSUE HOLDER TO LOAD FIRST TISSUE CONTAINER ~104

TAKE FIRST TISSUE SAMPLE AND DEPOSIT INTO FIRST TISSUE CONTAINER ~106

REMOVE FLUID BY DRAWING FLUID INTO THE PLATFORM OPENING AND FLUID CHANNEL ~108

ROTATE TISSUE HOLDER TO POSITION FIRST TISSUE CONTAINER AT IMAGING LOCATION ~110

TAKE IMAGE OF FIRST TISSUE SAMPLE ~112

ROTATE TISSUE HOLDER TO LOAD SECOND TISSUE CONTAINER ~114

TAKE SECOND TISSUE SAMPLE AND DEPOSIT INTO SECOND TISSUE CONTAINER ~116

REMOVE FLUID BY DRAWING FLUID INTO THE PLATFORM OPENING AND FLUID CHANNEL ~118

ROTATE TISSUE HOLDER TO POSITION SECOND TISSUE CONTAINER AT IMAGING LOCATION ~120

TAKE IMAGE OF SECOND TISSUE SAMPLE ~122

FIG. 13

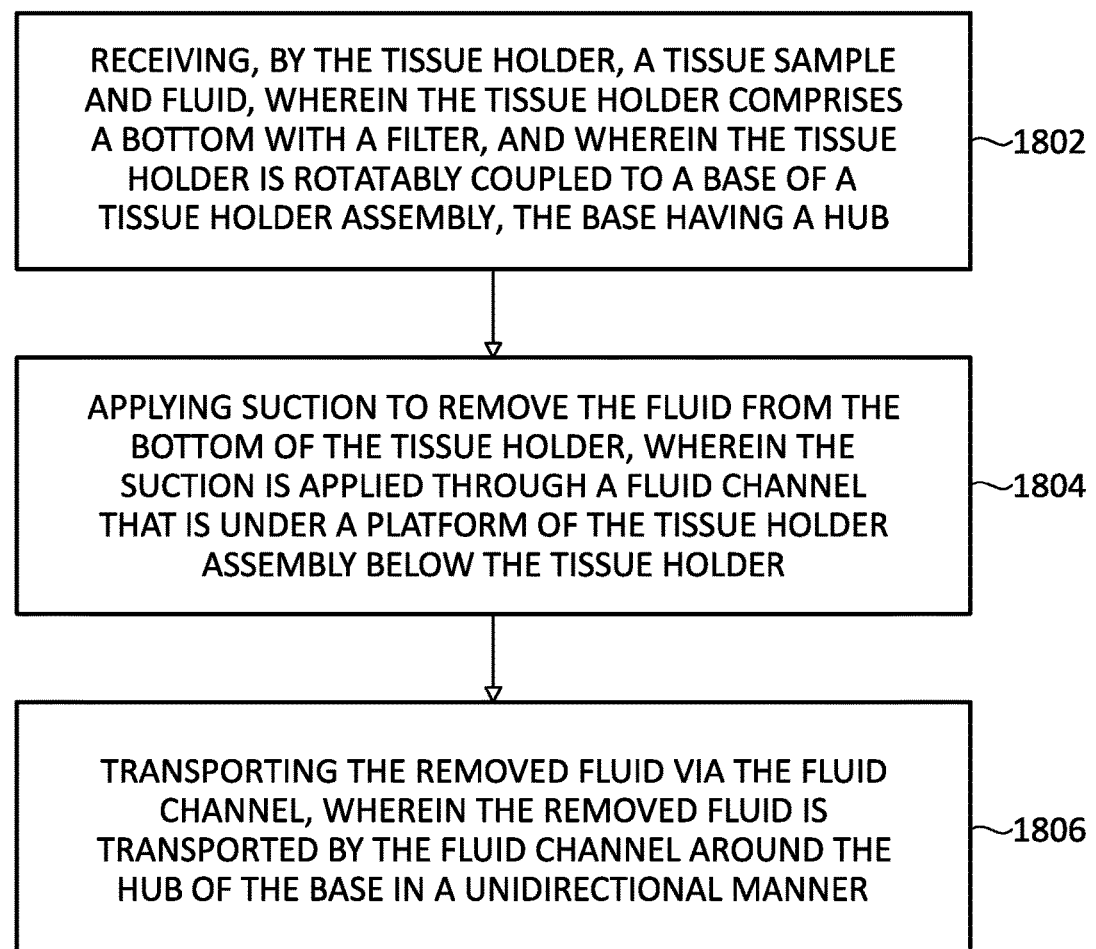

1800

RECEIVING, BY THE TISSUE HOLDER, A TISSUE SAMPLE AND FLUID, WHEREIN THE TISSUE HOLDER COMPRISES A BOTTOM WITH A FILTER, AND WHEREIN THE TISSUE HOLDER IS ROTATABLY COUPLED TO A BASE OF A TISSUE HOLDER ASSEMBLY, THE BASE HAVING A HUB ~1802

APPLYING SUCTION TO REMOVE THE FLUID FROM THE BOTTOM OF THE TISSUE HOLDER, WHEREIN THE SUCTION IS APPLIED THROUGH A FLUID CHANNEL THAT IS UNDER A PLATFORM OF THE TISSUE HOLDER ASSEMBLY BELOW THE TISSUE HOLDER ~1804

TRANSPORTING THE REMOVED FLUID VIA THE FLUID CHANNEL, WHEREIN THE REMOVED FLUID IS TRANSPORTED BY THE FLUID CHANNEL AROUND THE HUB OF THE BASE IN A UNIDIRECTIONAL MANNER ~1806

FIG. 18

APPARATUS AND ASSOCIATED METHODS FOR REDUCING FLUID IN BIOPSY TISSUE HANDLING SYSTEM FOR IMPROVING IMAGING QUALITY

RELATED APPLICATION DATA

This application is a National Stage Application of PCT/US2020/062181, filed on Nov. 25, 2020, which claims the benefit of priority under 35 U.S.C. § 119 to U.S. Provisional Application Ser. No. 62/941,395, filed on Nov. 27, 2019, the disclosures of which are hereby incorporated by reference in their entireties. To the extent appropriate, a claim of priority is made to each of the above disclosed applications.

FIELD

This disclosure generally relates to the preparation of biopsy tissue specimens for imaging, and more particularly, to devices and methods for reducing fluid in an imaging field of a biopsy tissue handling apparatus so that the fluid does not interfere with imaging a tissue sample in the tissue handling apparatus.

BACKGROUND

Biopsies are well-known medical procedures involving the removal of tissue from a living body and examining the tissue for diagnostic study, such as determining the presence, cause or extent of a disease. For example, a biopsy of human breast tissue may be performed for diagnosing breast cancer or other diseases. In general, a biopsy can be performed by either an open procedure or a percutaneous method. An open surgical biopsy procedure involves making an open incision to the site of the tissue of interest, cutting a sample of the tissue, and removing the tissue through the open incision. A percutaneous biopsy is performed by inserting a biopsy device having a needle and a cutting device through a small incision and advancing the needle and cutting device to the site of the tissue of interest. Then, the cutting device cuts a sample of tissue, and the biopsy device captures the tissue sample and removes the sample through the small incision. Percutaneous biopsy devices have used various means to remove the tissue sample, such as simply removing the device out through the incision with the captured tissue sample, or transporting the tissue sample out through the device (e.g., using a vacuum to aspirate the sample) where it can be removed or drawn through a tube to a container. One advantage of removing the tissue sample from the biopsy device is that multiple samples may be taken without having to remove the biopsy device.

The tissue sample is then examined for diagnosis by imaging the tissue sample using X-ray (while previous X-ray imaging systems recorded on film, more recent X-ray imaging system are digital and record using semiconductor receptors), MRI (magnetic resonance imaging) or other suitable imaging device. For instance, the tissue sample may be placed on an imaging substrate, such as a tissue slide or film, and then placed into the imaging device for taking an image.

Automated biopsy and imaging systems for performing a biopsy and imaging a tissue sample have also been disclosed. For example, U.S. Pat. No. 9,492,130 B2 discloses an integrated biopsy analysis system having a biopsy excision tool, a tissue sample transport mechanism for automatically transporting an excised tissue sample from the biopsy excision tool to an analysis/imaging unit, and an analysis/ imaging system for automatically analyzing tissue samples such as imaging using an X-ray imaging device. U.S. Pat. No. 9,492,130 B2 is hereby incorporated by reference herein in its entirety. The disclosed system excises tissue samples, and transfers and places the excised tissue samples into a specimen holder having a plurality of tissue accepting slots for placing a plurality of different tissue samples. The imaging unit is configured to acquire images of the tissue samples in the tissue holder, such as by acquiring individual images of each tissue sample in its respective tissue accepting slot.

SUMMARY

The integrated biopsy systems for performing a biopsy, described above, include a biopsy apparatus for taking a biopsy, as well as an imaging system for acquiring an image of each of the biopsied tissue samples. The excised tissue samples are individually transferred to a sample container of a tissue sample handling apparatus and are then imaged by the imaging system while in the tissue container. Various fluids are present during the process of excising the tissue sample and transporting the tissue sample from the biopsy site on the patient to the tissue sample handling apparatus. For example, bodily fluids such as blood, and surgical solutions such as saline, anesthetic, bio-fluids, etc. may be present at the location of the biopsy (or even flowing through the biopsy apparatus) when taking the tissue sample and/or drawing the tissue sample from the biopsy apparatus. Because the biopsy samples are transported from the biopsy site to the tissue sample handling apparatus through a fluid pathway (e.g., tubing, flow passages, etc.) by a vacuum, these fluids are deposited into the tissue sample handling apparatus along with the tissue samples.

It has been found that fluid in the imaging field (the area being imaged by an imaging device) interferes with the imaging process thereby reducing the quality of the image as compared to an image acquired without the fluid in the imaging field. For example, when acquiring an image using an imaging device, such as an X-ray imaging device, fluid droplets within the imaging field, such as fluid adhered to the bottom of a tissue sample holder, the bottom of a housing holding the tissue sample holder, or even on the surface of a cover above the tissue sample holder, show up as artifacts blocking the image of tissue of interest. The image of the specimen tissue can be used more effectively for diagnosis if the specimen tissue stands out with optimal contrast and sharpness from any surrounding structure of the container or surrounding fluid and that any tissue having characteristics indicative of cancer such as calcifications stand out from the normal tissue. For instance, artifacts in the image may include the container in which a tissue sample is being imaged and other background, such as fluids transmitted with the tissue sample. In addition to effective diagnosis, it is important to confirm that quality images are acquired for immediate assessment of the procedure, including accurate targeting of any lesion, and determining whether any additional samples need to be taken. Taking quality images further increases patient comfort by reducing the time the patient remains under compression during the biopsy procedure and reduces the possibility of needing the patient to return to repeat the procedure because the images were inadequate or incorrect tissue was recovered.

Accordingly, various embodiments of the herein disclosed inventions are directed to devices and methods for reducing fluid from the imaging field of the tissue handling apparatus, including keeping fluid from entering the imaging field and/or removing fluid that enters the imaging field.

A tissue holder assembly includes: a base, the base comprising a bottom member, a central hub extending upwardly from the bottom member, and a circumferential sidewall extending upwardly from the bottom member radially spaced apart from the hub, the circumferential sidewall surrounding the hub and defining an interior region configured for accommodating a cylindrical tissue holder; the base further comprising a raised platform spaced upwardly apart from the bottom member, an upper portion of the central hub extending through a central opening of the platform, wherein the hub is configured for supporting the tissue holder; the bottom member, the hub and the circumferential sidewall collectively defining an annular fluid channel underlying the platform, the fluid channel being in fluid communication with a platform opening; wherein the fluid channel extends around the hub from the platform opening to a fluid exit port in the circumferential sidewall; and wherein the base further comprises a flow comb underlying the platform opening and extending into the fluid channel.

Optionally, the flow comb has an arcuate shape.

Optionally, the flow comb comprises at least four flow channels.

Optionally, the flow comb comprises a hydrophobic coating and/or an anti-coagulant coating.

Optionally, the fluid channel is configured to provide unidirectional fluid flow around the hub through an angular range that is at least 180°.

Optionally, the fluid channel is configured to provide unidirectional fluid flow around the hub through an angular range that is 270°±20°.

Optionally, the hub of the base comprises a spindle configured to receive the tissue holder, and wherein the platform extends circumferentially around at least a majority of a space between the hub and the circumferential sidewall.

Optionally, the tissue holder assembly further includes a plenum in fluid communication with the fluid channel, and a suction port configured to provide suction in the plenum.

Optionally, the plenum is taller than the circumferential sidewall of the base.

Optionally, the tissue holder assembly further includes the tissue holder configured for placement in the interior region, the tissue holder having a plurality of tissue storage compartments, wherein a bottom of the tissue holder comprises a filter that allows fluid in one or more of the tissue storage compartments to pass therethrough.

Optionally, the tissue holder assembly further includes a cover configured to detachably attach to the base, wherein the cover comprises a tissue entry port configured to deliver tissue sample at a location that is above the platform opening.

Optionally, the flow comb has a length that is longer than a dimension of the platform opening measured along a longitudinal axis of the fluid channel.

A tissue holder assembly includes: a base, the base comprising a bottom member, a central hub extending upwardly from the bottom member, and a circumferential sidewall extending upwardly from the bottom member radially spaced apart from the hub, the circumferential sidewall surrounding the hub and defining an interior region configured for accommodating a cylindrical tissue holder; the base further comprising a raised platform spaced upwardly apart from the bottom member, an upper portion of the central hub extending through a central opening of the platform, wherein the hub is configured for supporting the tissue holder; the bottom member, the hub and the circumferential sidewall collectively defining an annular fluid channel underlying the platform, the fluid channel being in fluid communication with a platform opening; wherein the fluid channel extends around the hub from the platform opening to a fluid exit port in the circumferential sidewall; and wherein the tissue holder assembly further comprises a plenum located outside the circumferential sidewall, wherein the plenum is in fluid communication with the fluid channel, and is in fluid communication with a suction port configured to provide suction in the plenum.

Optionally, the suction port is located at one end of the plenum.

Optionally, the plenum is taller than the circumferential sidewall of the base.

Optionally, the suction port is also configured to provide suction in the fluid channel.

Optionally, the fluid channel is configured to provide unidirectional fluid flow around the hub through an angular range that is at least 180°.

Optionally, the fluid channel is configured to provide unidirectional fluid flow around the hub through an angular range that is 270°±20°.

Optionally, the hub of the base comprises a spindle configured to receive the tissue holder, and wherein the platform extends circumferentially around at least a majority of a space between the hub and the circumferential sidewall.

Optionally, the tissue holder assembly further includes a flow comb below the platform opening, the flow comb extending inside the fluid channel.

Optionally, the flow comb has a length that is longer than a dimension of the platform opening measured along a longitudinal axis of the fluid channel.

A tissue holder assembly includes: a base, the base comprising a bottom member, a central hub extending upwardly from the bottom member, and a circumferential sidewall extending upwardly from the bottom member radially spaced apart from the hub, the circumferential sidewall surrounding the hub and defining an interior region configured for accommodating a cylindrical tissue holder; the base further comprising a raised platform spaced upwardly apart from the bottom member, an upper portion of the central hub extending through a central opening of the platform, wherein the hub is configured for supporting the tissue holder; the bottom member, the hub and the circumferential sidewall collectively defining an annular fluid channel underlying the platform, the fluid channel being in fluid communication with a platform opening; wherein the fluid channel extends around the hub from the platform opening to a fluid exit port in the circumferential sidewall, to thereby provide unidirectional fluid flow around the hub of the base.

Optionally, the fluid channel is configured to provide the unidirectional fluid flow around the hub through an angular range that is at least 180°.

Optionally, the fluid channel is configured to provide the unidirectional fluid flow around the hub through an angular range that is 270°±20°.

Optionally, the tissue holder assembly further includes a flow comb below the platform opening, the flow comb extending inside the fluid channel.

Optionally, the flow comb has an arcuate shape.

Optionally, the flow comb comprises at least four flow channels.

Optionally, the flow comb has a length that is longer than a dimension of the platform opening measured along a longitudinal axis of the fluid channel.

Optionally, the tissue holder assembly further includes a plenum, wherein the fluid channel is in fluid communication with the plenum.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

FIG. 13 illustrates a flow chart of a method for using and/or operating the tissue holder assembly of FIG. 1;

FIG. 18 illustrates a method of removing fluid from a tissue holder.

DETAILED DESCRIPTION

Figure 1:
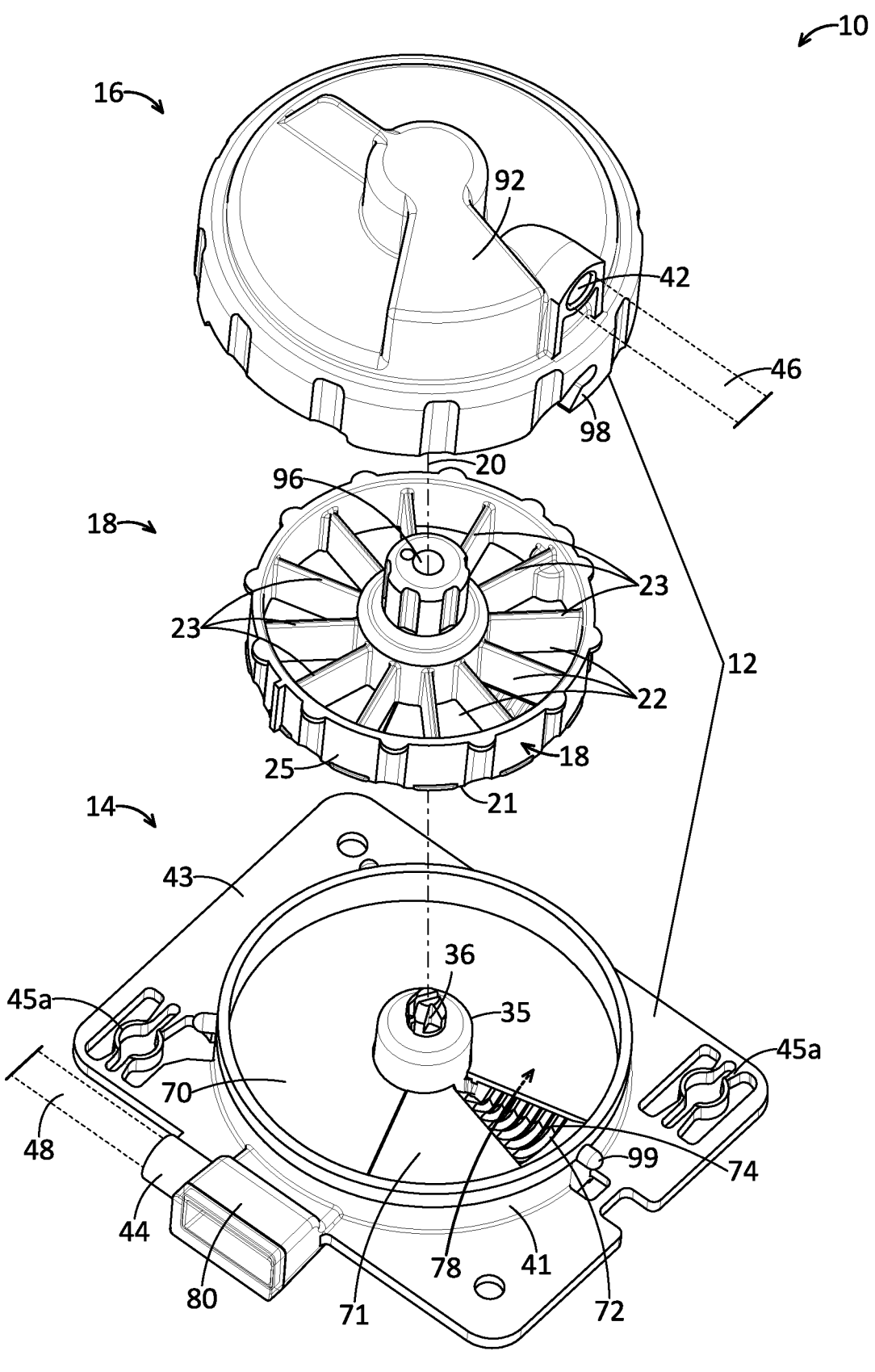
FIG. 1 illustrates components of a tissue holder assembly having a base, a cover, and a tissue holder.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Figures 2, 3:
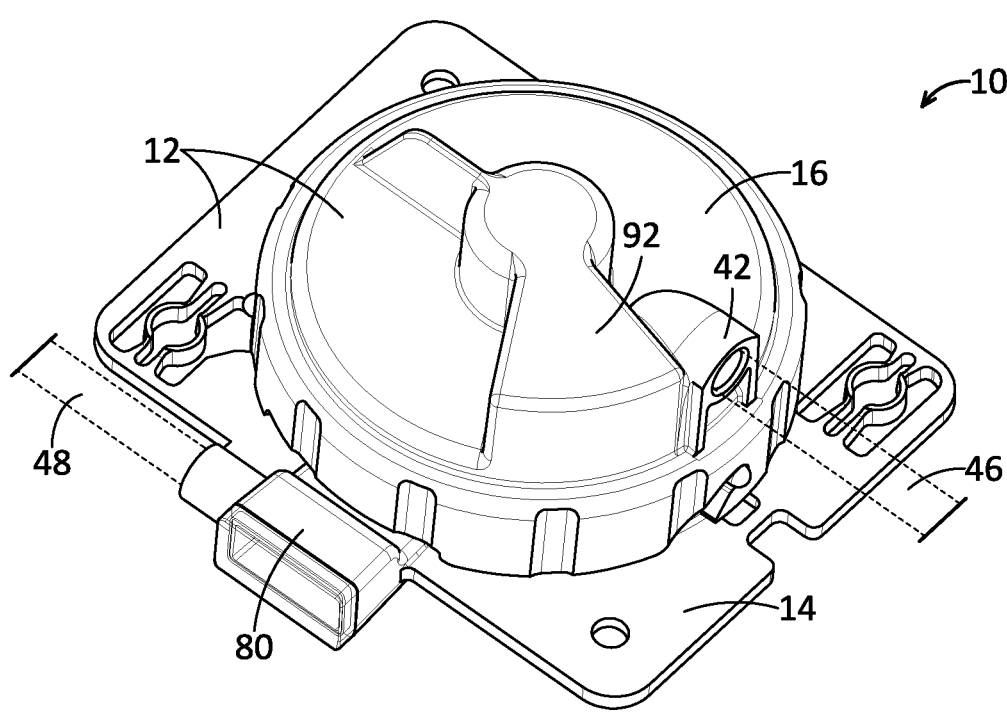
FIG. 2 illustrates the tissue holder assembly of FIG. 1 as assembled.
FIG. 3 illustrates the tissue holder of FIG. 1.

FIGS. 1-3 illustrate one embodiment of a tissue holder assembly 10 for receiving a plurality of tissue samples. The tissue holder assembly 10 includes a housing 12 having a base 14 and a cover 16 which removably attaches onto the base 14. The base 14 and attached cover 16 form an interior or chamber in which a tissue holder 18 is enclosed. The base 14 has a hub 35 with a spindle 36 which receives a hub 38 of the tissue holder 18, such that the tissue holder 18 is rotatable relative to the housing 12 about an axis 20. In other words, the base 14 and cover 16 remain stationary and the tissue holder 18 rotates within the chamber formed by the base 14 and cover 16. The tissue holder 18 may be rotated using any suitable actuator, and may include a magnet that is detected by a hall effect sensor to identify when the tissue filter is in a home position.

The base 14 has a bottom member 43 and a circumferential sidewall 41 extending upward from the bottom member 43. The bottom member 43 may comprise a substantially flat plate. The bottom member 43 has a plurality of retaining clips 45a, 45b which removably attach to mating retainers on a chassis, frame, housing, or the like, of a tissue biopsy system 50 (see FIGS. 1 and 4). A spindle 36 is attached to the bottom member 43 and extends upward from the bottom member 43. The tissue holder 18 has a bottom 21 and a circumferential sidewall 25 extending upward from the bottom 21. The tissue holder 18 has a plurality of tissue storage compartments 22 (in this case, the tissue holder 18 has 13 tissue storage compartments 22, but any number of compartments 22 can be used) arranged angularly around the tissue holder 18. The tissue storage compartments 22 are defined by radial dividing walls 23 extending radially from the hub 38 to the sidewall 25. The tissue storage compartments 22 (also referred to as tissue containers 22) are separated, and partially formed, by radially extending compartment walls 23. In this exemplary embodiment, the tissue holder 18 has a circular shape such that the tissue storage compartments 22 are wedge-shaped (i.e., pie-shaped, sector of a circle), or a sector of an annulus shape in the case that the central part of each tissue storage compartment 22 does not extend all the way to the axis 20. The tissue containers 22 connect to the hub 38 of the tissue holder 18 that is centrally located at the axis 20. The hub 38 is circular and has an opening that allows the spindle 36 of the base 14 to fit through the opening.

The bottom 21 of the tissue holder 18 has a tissue filter 24 comprising a porous filter material. The tissue filter 24 may be a single filter, such as a filter sheet, which covers the entire bottom of the tissue holder 18. Alternatively, the tissue filter 24 may be individual filters disposed on the bottom of each tissue storage compartment 22.

The tissue holder assembly 10 also includes a platform 70 with a platform opening 72, and a fluid channel 78 located below the platform 70 (see dashed arrow pointing to the fluid channel 78 below the platform 70). The platform 70 has a planar horizontal surface. In some embodiments, the bottom of the tissue holder 18 may rest on the planar horizontal surface of the platform 70 as the tissue holder 18 rotates relative to the base 14. In other embodiments, the bottom of the tissue holder 18 may be spaced away from the planar horizontal surface of the platform 70 by a small distance, such as less than 0.5 mm, less than 0.2 mm, less than 0.1 mm, or less than 0.05 mm. The platform 70 extends around the hub 35. In particular, the platform has a central opening that allows an upper portion of the hub to extend therethrough. The fluid channel 78 extends circumferentially around the hub 35 of the base 14 underneath the platform 70, and is in fluid communication with a plenum 80 at the base 14. A suction line 48 is coupled to the plenum 80 for applying suction inside the plenum 80 and the fluid channel 78. The tissue holder assembly 10 also includes flow comb 74 below the platform opening 72. In some embodiments, the flow comb 74 may extend from the platform opening 72 into the fluid channel 78. During use, fluid from the tissue holder 18 is drawn into the platform opening 72 due to suction in the fluid channel 78 applied by the suction line 48. The flow comb 74 breaks up the fluid, and the fluid is transported by the fluid channel 78 around the hub 35 to reach the plenum 80. The plenum 80 allows a certain amount of fluid to be collected while fluid is being suctioned by the suction line 48 out of the plenum 80 via the outlet port 44 (also referred to as a vacuum port 44). In some embodiments, the outlet port 44 has an inner diameter of 0.26 inch. In other embodiments, the outlet port 44 may have an inner diameter of other dimensions, which may be larger than 0.26 inch or smaller than 0.26 inch.

The fluid channel 78 may extend circumferentially around the hub 35, such that the fluid in the fluid channel 78 of the base 14 will travel an angular distance circumferentially around the hub 35 to reach the plenum 80. As shown in FIG. 1, fluid channel 78 extends about 270° circumferentially about the hub 35 and travels an angular distance of about 270° to reach the plenum 80. It is understood that the plenum may be located at any other point along the fluid pathway, and that the fluid channel 78 may extend through other angular ranges. For example, in other embodiments, the fluid channel 78 may extend around the hub 35 through an angle that is at least 30° and at most 300°. Also, in the illustrated embodiments, the platform 70 extends circumferentially around a majority of a space between the hub 35 and the circumferential sidewall 41. In other embodiments, the platform 70 may extend around the hub 35 by a range that is different from that illustrated and/or may include perforations, holes, and/or slits to allow liquid to pass through platform 70 into the fluid channel.

As shown in FIG. 1, the tissue holder assembly 10 also includes an imaging platform 71 that corresponds with an imaging position for imaging tissue samples. The tissue holder assembly 10 includes an imager located under the imaging platform 71. In particular, when a tissue sample in the tissue holder 18 is placed above the imaging platform 71, imaging may then be performed by the imager underneath the imaging platform 71 to image the tissue sample. In some embodiments, the imaging platform 71 is a molded piece having solid walls that is raised above the bottom member 43 to prevent fluid from collecting in and around an imaging area. During use, one of the tissue storage compartments 22 containing tissue sample to be imaged is placed above the imaging platform 71. In some cases, the filter 24 at the bottom of the tissue holder 18 may sit flush on the imaging platform 71. It should be noted that the imaging platform 71 is a separate piece from the platform 70, and does not define any fluid channel.

As shown in FIG. 1, the cover 16 also includes a raised portion 92 that defines a vaulted compartment corresponding to an imaging position of tissue samples. In particular, when one of the tissue storage compartments 22 containing tissue sample is placed below the raised portion 92 and above the surface 71, imaging may then be performed to image the tissue sample. The cover 92 also includes an anchor 98 configured to engage with protrusion 99 at the circumferential sidewall 41 of the base 14. To lock the cover 16 against the base 14, the cover 16 may be placed over the base 14 to cover the circumferential sidewall 41, and the cover 16 may then be rotated relative to the base 14 to place the anchor 98 around the protrusion 99, thereby locking the cover 16 against the base 14. In the illustrated embodiments, there are two anchors 98 on opposite sides of the cover 16 for mating with respective protrusions 99 on opposite sides of the circumferential sidewall 41. In other embodiments, there may be more than two anchors 98 or only one anchor 98. Similarly, in other embodiments, there may be more than two protrusions 99 on only one protrusion 99.

In some embodiments, the platform opening 72, the fluid channel 78, and the flow comb 74 may be considered as parts of a fluid removal mechanism. The fluid removal mechanism is configured for removing fluid from the filter 24 underlying the bottom of a plurality of tissue storage compartments 22 in order to improve the quality of images acquired of tissue samples in the tissue storage compartments. In other embodiments, the structures that participate in defining the fluid channel 78 may also be considered to be parts of the fluid removal mechanism. For example, the platform 78 above the fluid channel 78, a bottom member of the base 14 below the fluid channel 78, or both, may be considered to be parts of the fluid removal mechanism. In further embodiments, the plenum 80, the suction line 48, or both, may be considered to be parts of the fluid removal mechanism.

Figure 4:
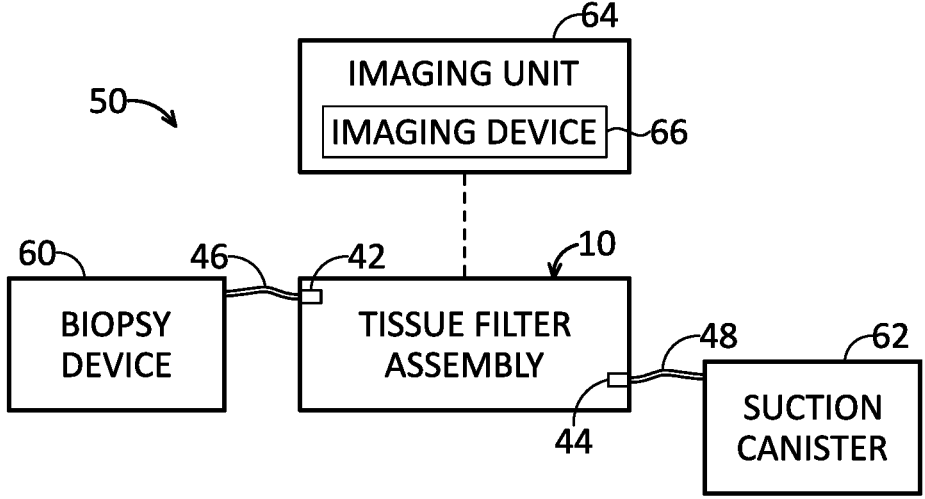
FIG. 4 is a schematic view of a biopsy system comprising the tissue holder assembly of FIG. 1.

The tissue holder assembly 10 has a tissue sample entry port 42 (also referred to as inlet port 42) at the cover 16 to which an inlet tube 46 is connected (see FIGS. 1 and 4). The other end of the inlet tube 46 is connected to a biopsy excision tool 60 (see FIG. 4) such that tissue samples excised by the biopsy excision tool 60 are transported from the biopsy excision tool 60 through the inlet tube 46, into the tissue holder assembly 10 and into one of the tissue storage compartments 22. The outlet port 44 of the tissue holder assembly 10 is connected to the suction tube 48. The other end of the suction tube 48 is connected to the suction canister 62 or another suitable vacuum source (see FIG. 4). The vacuum port 44 draws liquid and/or other material, via the fluid channel 78 and the plenum 80, out of the base 14, and also provides a vacuum within the chamber formed by the housing 12 for drawing tissue samples through the inlet port 42 to be deposited in the respective tissue storage compartments 22 of the tissue holder 18.

Referring to FIG. 4, a schematic of a tissue biopsy system 50 is shown. While the schematic of FIG. 4 only shows certain features of the biopsy system 50, the biopsy system 50 may be the biopsy system as disclosed in U.S. Pat. No. 9,492,130 B2, referenced above, and may include any of the features disclosed therein. The biopsy system 50 includes the tissue holder assembly 10, attached to a biopsy excision tool 60 and a suction canister 62. The biopsy system 50 also includes an imaging unit 64 configured to capture images of tissue samples contained in each of the tissue storage compartments 22. The imaging unit 64 has an imaging device 66, such as an X-ray imaging device 66, or other suitable imaging device for capturing images. The imaging device 66 has an imaging field in which the imaging device 66 can acquire an image of material positioned in the imaging field.

Figure 5:
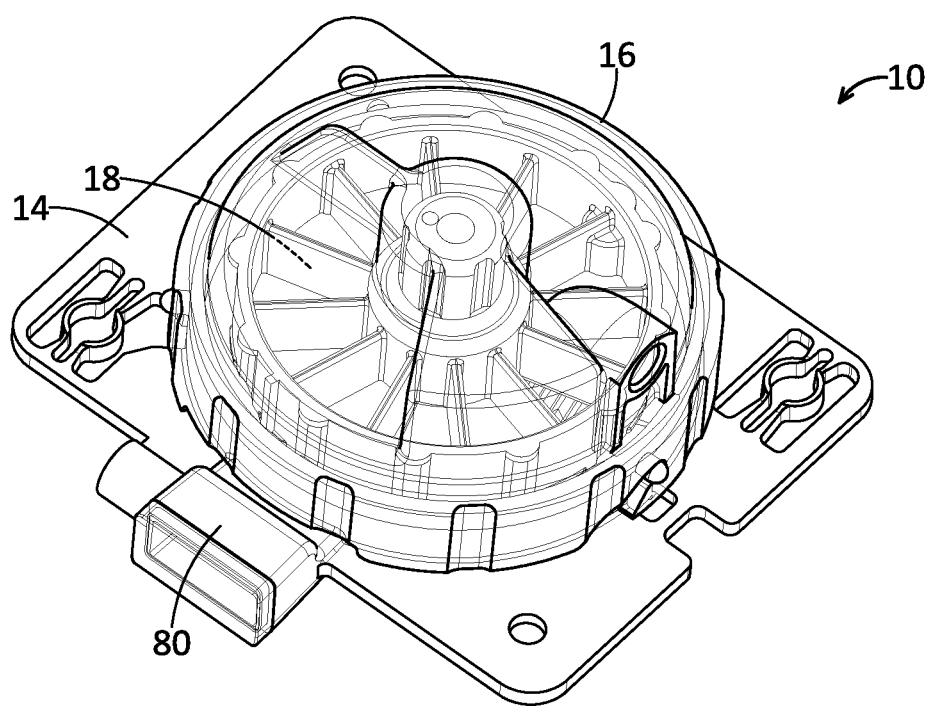
FIG. 5 illustrates a partial transparent view of the tissue holder assembly of FIG. 1.
Figure 6:
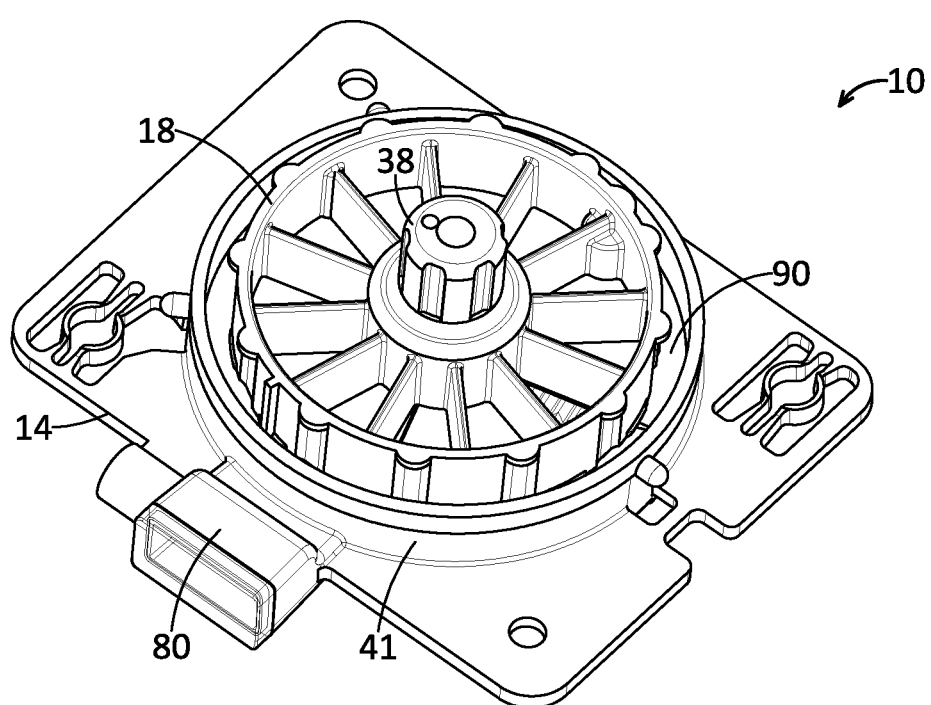
FIG. 6 illustrates the tissue holder assembly of FIG. 1, without the cover of the tissue holder assembly.
Figure 7:
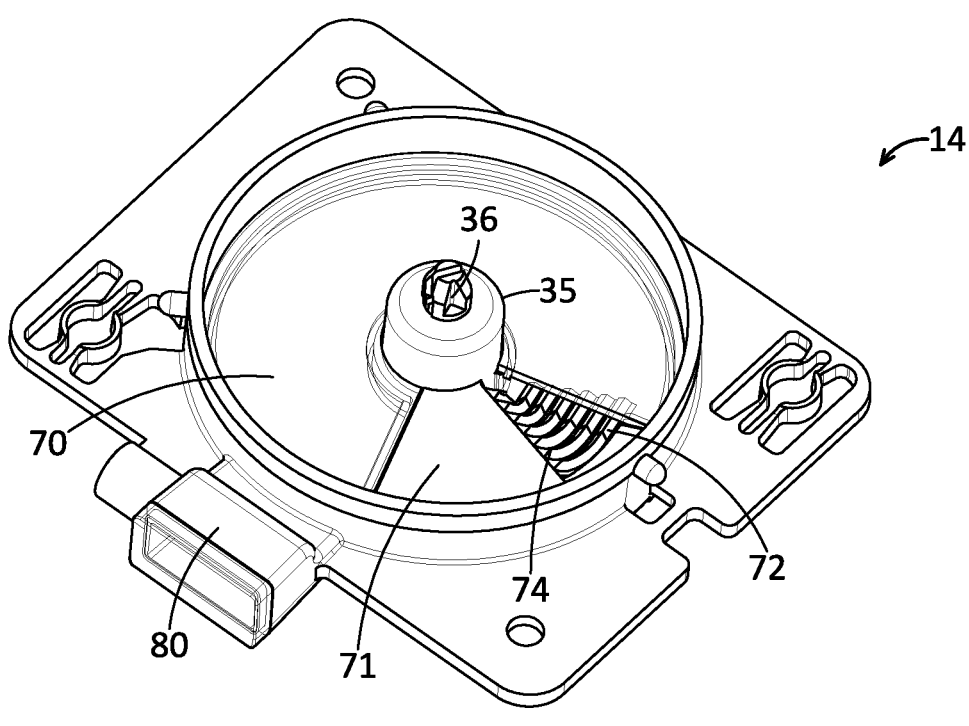
FIG. 7 illustrates a partial transparent view of the base of the tissue holder assembly of FIG. 1.

The tissue holder assembly 10 of will now be described in further details with references to FIGS. 5-12. FIG. 5 illustrates a partial transparent view of the tissue holder assembly 10 of FIGS. 1-2. As shown in the figure, the cover 16 is illustrated as being partially transparent so that the tissue holder 18 under the cover 14 can be seen. FIG. 6 illustrates the tissue holder assembly 10, with the cover 16 removed. As shown in the figure, the circumferential sidewall 41 of the base 14 defines a space for accommodating the tissue holder 18. When the tissue holder 18 is rotatably coupled to the base 14, the tissue holder 18 is separated from the circumferential sidewall 41 of the base 14 by a gap 90. This allows the tissue holder 18 to rotate relative to the base 14 without interference. FIG. 7 illustrates the base 14 of the tissue holder assembly 10 with the cover 16 and the tissue holder 18 removed. As shown in the figure, the platform 70 of the base 14 of the tissue holder assembly 10 is presented in a partial transparent format in order to illustrate a part of the flow comb 74 underneath the platform 70.

Figure 8:
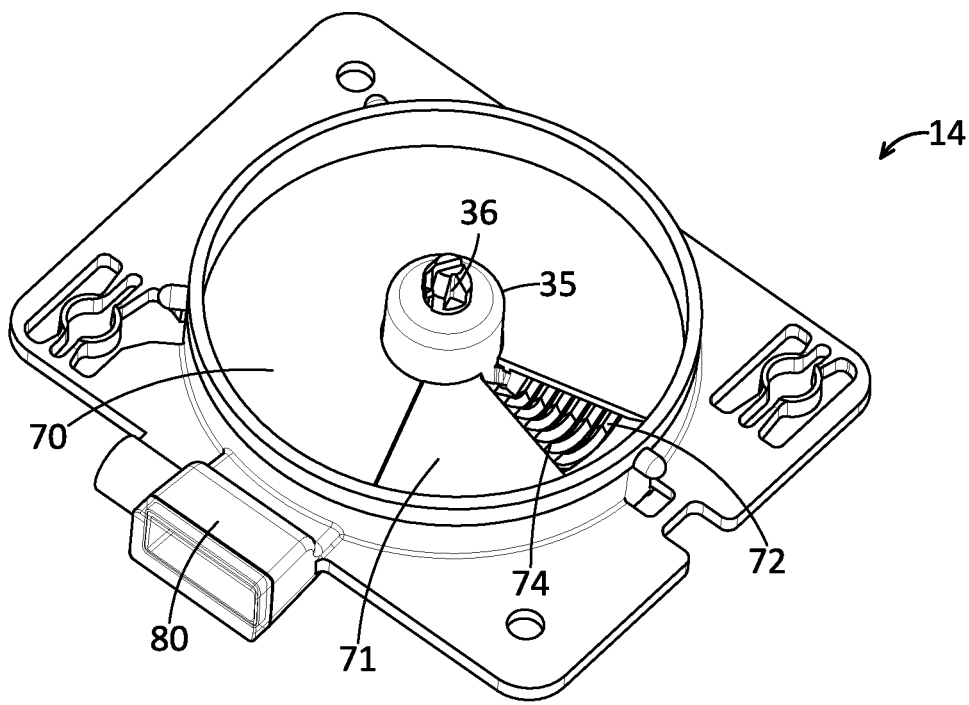
FIG. 8 illustrates the base of the tissue holder assembly of FIG. 1, particularly showing the base having a platform.

FIG. 8 illustrates the base 14 of the tissue holder assembly 10, without the partial transparent representation of the platform 70. In the illustrated embodiments, the platform opening 72 is formed between one end of the platform 70, and the imaging platform 71. In other embodiments, the platform opening 72 may be formed within the platform 70 without utilizing the imaging platform 71.

Figure 9:
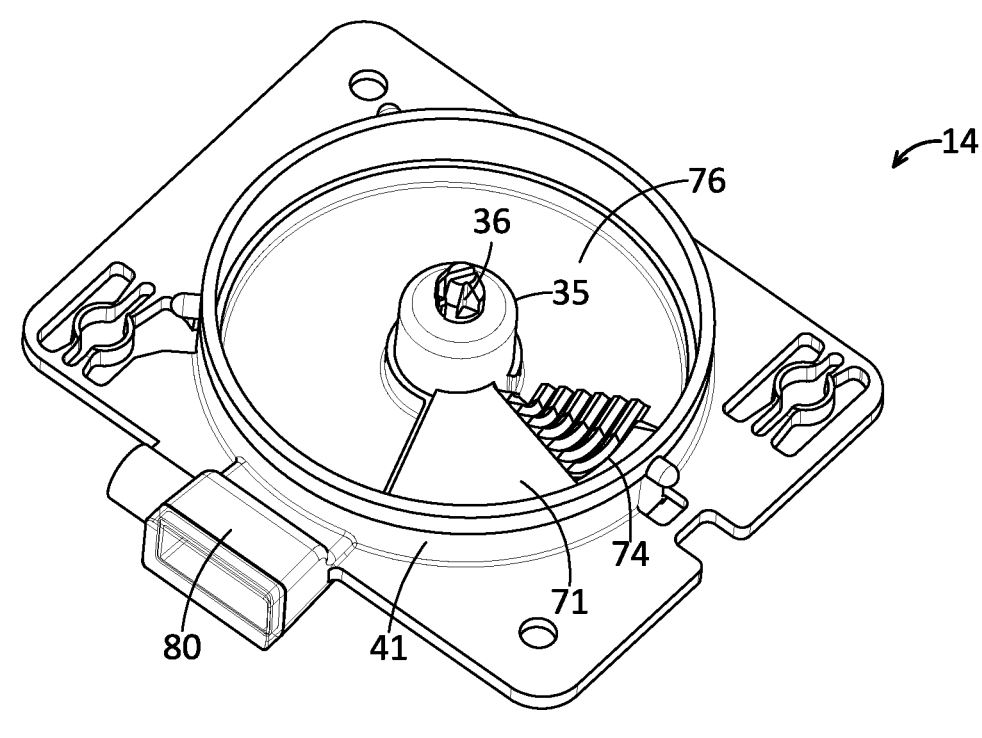
FIG. 9 illustrates the base of FIG. 8, particular, showing the platform of the base removed.

FIG. 9 illustrates the base 14 of the tissue holder assembly 10, particular, showing the platform 70 removed from the base 14. The imaging platform 71 and the extent of the flow comb 74 can be seen. As shown in the figure, the base 14 includes a bottom member 76 surrounded by the circumferential sidewall 41 of the base 14. The bottom member 76 has an elevation that is below that of the flow comb 74. In some embodiments, the imaging platform 71 and/or the flow comb 74 may be molded together with the bottom member 76 of the base 14. As shown in the figure, the flow comb 74 has an arcuate shape, which allows fluid to be transported along a curvilinear path from the platform opening 72 into the fluid channel 78. In the illustrated embodiments, the flow comb 74 has six parallel flow channels 75. In other embodiments, the flow comb 74 may have more than six parallel flow channels 75 (e.g., seven, eight, nine channels, etc.), or fewer than six flow channels 75 (e.g., five, four, three, two channel). In some cases, the flow comb 74 may include at least four flow channels. Also, in the illustrated embodiments, the flow comb 74 has a length that is longer than a dimension of the platform opening 72 measured along a longitudinal axis of the fluid channel 78. In other embodiments, the flow comb 74 has a length that is shorter than, or the same as, a dimension of the platform opening 72 measured along a longitudinal axis of the fluid channel 78. Furthermore, in the illustrated embodiments, a first part of the flow comb 74 adjacent the platform opening 72 may have a first slope that is approximately vertical (e.g., 90°±20°), a second part of the flow comb 74 following the first part may have a second slope that is approximately 45°±20°, and a third part of the flow comb 74 following the second part and extending inside the fluid channel 78 may have a third slope that is approximately 0°±20°. In other embodiments, the flow comb 74 may have other sloping profiles. In some embodiments, surface treatment may be applied to the flow comb 74 to assist in flow of fluid over the flow comb 74. For example, in some embodiments, anti-coagulant coating, hydrophobic coating, or other treatments may be applied on the surface of the flow combs 74.

Figure 10:
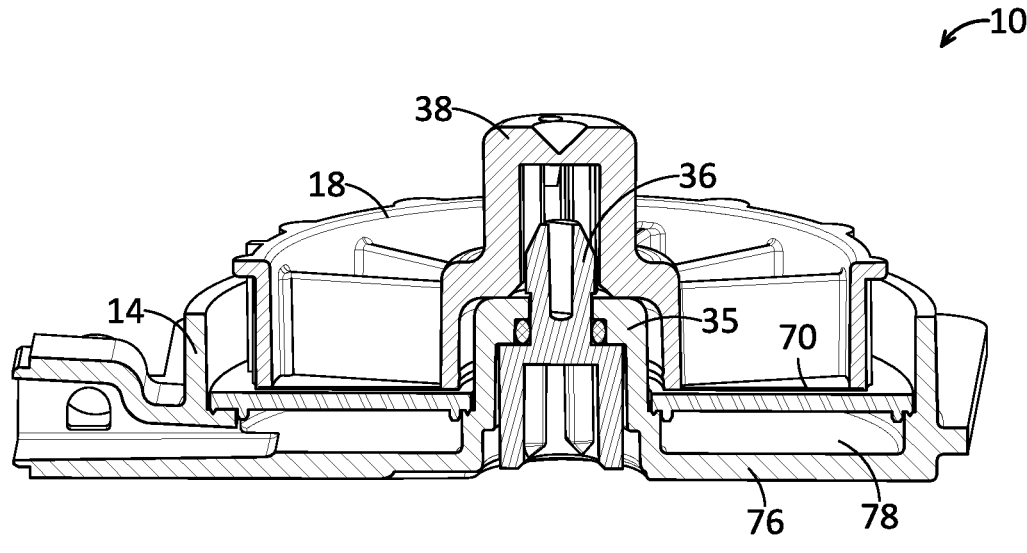
FIG. 10 illustrates a partial cut-away view of the tissue holder assembly of FIG. 1, without the cover of the tissue holder assembly.

As shown in FIG. 10, the bottom member 76 and the platform 70 together define a fluid channel 78. The platform 70 and the fluid channel 78 are located below the tissue holder 18 when the tissue holder 18 is coupled to the base 14. The fluid channel 78 is configured to provide suction for transporting fluid through the fluid channel 78. As used in this specification, the term "fluid channel" may be any passage that is capable of transporting fluid, such as gas (e.g., air) and/or liquid.

Figure 11:
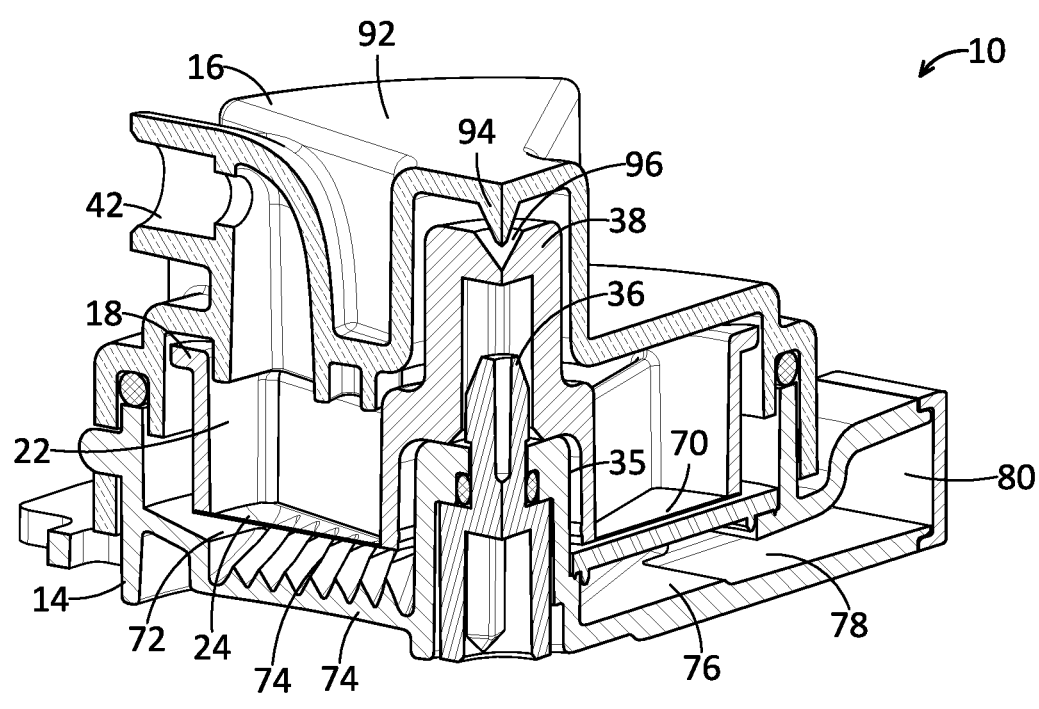
FIG. 11 illustrates another partial cut-away view of the tissue holder assembly of FIG. 1.

FIG. 11 illustrates a partial cut-away view of the tissue holder assembly 10, particularly showing the tissue holder 18 having been loaded inside the interior defined by the base 14 and the cover 16. The cover 16 of the tissue holder assembly 10 includes a protrusion 94 configured to mate with an opening 96 at the hub 38 of the tissue holder 18. The lower part of the hub 38 of the tissue holder 18 has an opening for receiving the hub 35 of the base 14. The hub 38 also has a slot for receiving the spindle 36 of the base 14. Rotation of the spindle 38 will cause the tissue holder 18 to rotate relative to the base 14. The protrusion 94 from the cover 16 and the hub 35 of the base 14 extend into the hub 38 of the tissue holder 18 from opposite directions, thereby stabilizing the tissue holder 18 while it is being rotated by the spindle 36. Accordingly, the tissue holder 18 is removably coupled to the spindle 36 (drive member) at the base 14, and is configured to be selectively rotated by the spindle 36 about an axis that is substantially orthogonal (e.g. 90°±10°) with respect to the bottom member 76.

As shown in FIG. 11, the inlet port 42 at the cover 16 is radially aligned with a respective tissue storage compartment 22, and is also radially aligned with the platform opening 72 formed at least partially with the platform 70. Accordingly, when tissue sample with fluid is delivered into the inlet port 42, the tissue sample and the fluid will be deposited into the respective tissue storage compartment 22. The tissue sample will be contained by the filter 24 at the bottom of the tissue holder 18, while fluid will exit through the filter 24, and will go through the platform opening 72 of the platform 70. During use of the tissue holder assembly 10, suction will be provided inside the fluid channel 78 to help draw fluid from the bottom of the tissue holder 18 into the platform opening 72.

Figure 12:
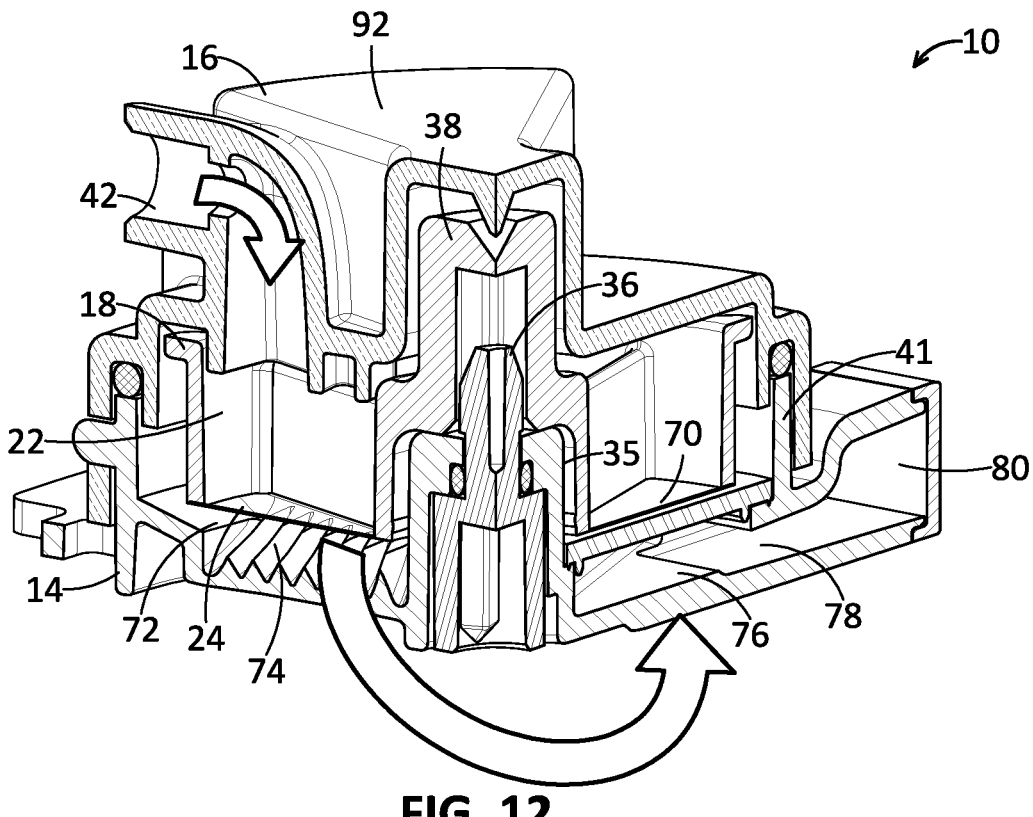
FIG. 12 illustrates the partial cut-away view of the tissue holder assembly of FIG. 11, particularly showing fluid flow direction.

FIG. 12 illustrates the partial cut-away view of the tissue holder assembly 10 of FIG. 11, particularly showing fluid flow direction. As shown, a tissue sample and fluid from the biopsy device 60 (shown in FIG. 4) enters into the tissue holder assembly 10 via the inlet port 42. The tissue sample is deposited into one of the tissue storage compartments 22 in the tissue holder 18. The filter 24 at the bottom of the tissue holder 18 prevents the tissue sample from exiting through the bottom of the tissue holder 18, while allowing the fluid to pass therethrough. Due to suction provided in the fluid channel 78, fluid enters into the platform opening 72 at the platform 70, and is broken up by the flow comb 74 inside the fluid channel 78. The fluid is then transported, due to the suction force inside the fluid channel 78, through the fluid channel 78, and exits via an exit port 97 at the circumferential sidewall 41 of the base into the plenum 80. The plenum 80 allows a certain amount of fluid to be collected while fluid is being suctioned out of the plenum 80 via the outlet port 44 (shown in FIG. 1) into suction line 48.

With reference to FIG. 13, a method 100 of using and operating the tissue holder assembly 10 will now be described. At item 102, the tissue holder assembly 10 is installed into an automated biopsy system 50, such as a system as described in U.S. Pat. No. 9,492,130 B2, described above, with the biopsy excision tool 60 connected to the inlet tube 46, and a vacuum source connected to the suction tube 48. The tissue holder assembly 10 or just the tissue holder 18 (e.g., a tissue holder 18 may be installed into the tissue holder assembly which is installed in the system 50) may be manually installed in the automated biopsy system 50, or the system 50 may include a robot which is configured to automatically install the tissue holder assembly 10 or just the tissue holder 18 into the system 50.

At item 104, the tissue holder 18 is rotated to position a first tissue storage compartment 22 at a loading position of the tissue filter holder 18 such that a tissue sample transported through the inlet port 42 will be deposited into the first tissue storage compartment 22 of the tissue holder 18. When the first tissue storage compartment 22 is at the loading position, it is also above the platform opening 72.

At item 106, a first tissue sample is excised using the biopsy excision tool 62, and the first tissue sample is transported through the inlet tube 46 and inlet port 42 and is deposited into the first tissue storage compartment 22 of the tissue holder 18.

At item 108, fluid remnants accumulated on the bottom surface of the filter 24 underlying the first tissue storage compartment 22 is removed. In particular, suction is applied in the fluid channel 78 to draw fluid at the bottom of the first tissue storage compartment 22 into the platform opening 72. The fluid is then transported via the fluid channel 78 to the plenum 80, and is suctioned out of the plenum 80 via the suction line 48. The flow of fluid in item 108 may occur in the manner shown in FIG. 12. In the illustrated embodiments, fluid is transported counterclockwise in the fluid channel 78 from the channel opening 72 to reach the plenum 80. In other embodiments, the position of the plenum 80 relative to the platform opening 72 may be changed, and the configuration of the flow comb 74 may be flipped so that fluid is transported clockwise in the fluid channel 78 from the channel opening 72 to reach the plenum 80.

Returning to FIG. 13, at item 110, the first tissue storage compartment 22 is positioned in the imaging field of the imaging unit 64 to acquire an image of the first tissue sample in the first tissue storage compartment 22. The imaging field may be located adjacent the platform opening 72. In the illustrated embodiments, after suction is applied to remove fluid at the bottom of the first tissue storage compartment 22 (when the first tissue storage compartment 22 is at the loading position), the tissue holder 18 may be rotated clockwise to move the first tissue storage compartment 22 from the loading position, which is above the platform opening 72, to an imaging position that is above the surface 71. Thus, in some embodiments, fluid travels in the fluid channel 78 in a counterclockwise direction, and the tissue holder 18 rotates in a clockwise direction.

Alternatively, the tissue holder 18 may rotate in a counterclockwise direction.

At item 112, an image of the first tissue sample is acquired using the imaging unit 64.

At item 114, the tissue holder 18 is rotated to position a second tissue storage compartment 22 at the loading position of the tissue holder 18 such that a tissue sample transported through the inlet port 42 can be deposited into the second tissue storage compartment 22. This positioning may occur during the same movement as item 110. In other words, as the first tissue storage compartment 22 is moved to the imaging position, the second tissue storage compartment 22 may be positioned at the loading position. When the second tissue storage compartment 22 is at the loading position, it is above the platform opening 72.

At item 116, a second tissue sample is excised using the biopsy excision tool 60, and the second tissue sample is transported through the inlet tube 46 and inlet port 42 and is deposited into the second tissue storage compartment 22 of the tissue holder 18.

At item 118, fluid remnants accumulated on the bottom surface of the filter 24 underlying the second tissue storage compartment 22 is removed. In particular, suction is applied in the fluid channel 78 to draw fluid at the bottom of the second tissue storage compartment 22 into the platform opening 72. The fluid is then transported via the fluid channel 78 to the plenum 80, and is suctioned out of the plenum 80 via the suction line 48. The flow of fluid in item 108 may occur in the manner shown in FIG. 12.

Returning to FIG. 13, at item 120, the second tissue storage compartment 22 is positioned in the imaging field for the imaging unit 64 to acquire an image of the second tissue sample in the second tissue storage compartment 22. Again, the imaging field may be located just past the platform opening 72.

At item 122, an image of the second tissue sample is acquired using the imaging unit 64. The process is repeated until all of the desired tissue samples have been obtained, deposited into a tissue storage compartment 22 and images have been acquired for all of the respective tissue samples in each of the tissue storage compartments 22.

Alternatively, images of the tissue samples in the tissue storage compartments 22 may be acquired after all the samples are acquired. First, all of the tissue samples are obtained and deposited into respective tissue storage compartments 22 by rotating each tissue storage compartment 22 to the loading position, excising a tissue sample, and depositing the tissue sample into its respective tissue storage compartment 22. Then, the tissue holder 18 is rotated to remove the fluid from each of the tissue containers 22 in the tissue holder 18 and the tissue samples in the tissue holder assembly 10 are imaged. The tissue samples may be imaged all at once by taking a single image of all the tissue containers 22 in the tissue holder 18, processing the image to identify the individual containers 22 and separating each image from each container 22. Alternatively, the tissue holder 18 may be rotated to acquire a separate image of each of the containers until images have been taken of all of the respective tissue samples in each of the tissue containers 22. In yet another embodiment, the tissue holder assembly 10 is placed in an imaging unit, such as an X-ray imaging device. In a manual system, the filter assembly 10 may be manually installed in the imaging unit 54.

In an automated and integrated system such as the system described above, the tissue holder assembly 10 is already located in the imaging unit 64 while performing the biopsy excisions, or a robot may place the tissue holder assembly 10 in the imaging unit 64. The tissue holder 18 is then rotated to move a tissue storage compartment 22 across the platform opening 72 for fluid removal, the tissue storage compartment 22 is positioned in the imaging position, and an image is acquired using the imaging unit 64. This process is repeated for each of the tissue storage compartments 22 having a tissue sample to be imaged.

It should be noted that the platform 70 of the fluid removal system is advantageous because it keeps fluid below it and shields the tissue holder 18 from fluid. Without the platform 70, fluid may splash onto the image platform 71 as the fluid enters the fluid holder assembly 10 and during transport of the fluid. In addition, the platform 70 is advantageous because it prevents the housing 12 from filling up with fluid during use. Without the platform 70, excess fluid may accumulate within the housing 12, and may rise to a level that would cause the tissue samples in the tissue holder 18 to float. Also, running the fluid channel 78 at least partially around the hub 35 of the base 14 is advantageous because it provides a channel length that may allow some collection of fluid, and may prevent over accumulation of fluid. In addition, the flow comb 74 is advantageous because it breaks up fluid into finer droplets for allowing easier suction of the fluid by the suction force inside the fluid channel 78. The flow comb 74 also allows fluid to flow easier inside the channel 78.

Figure 14:
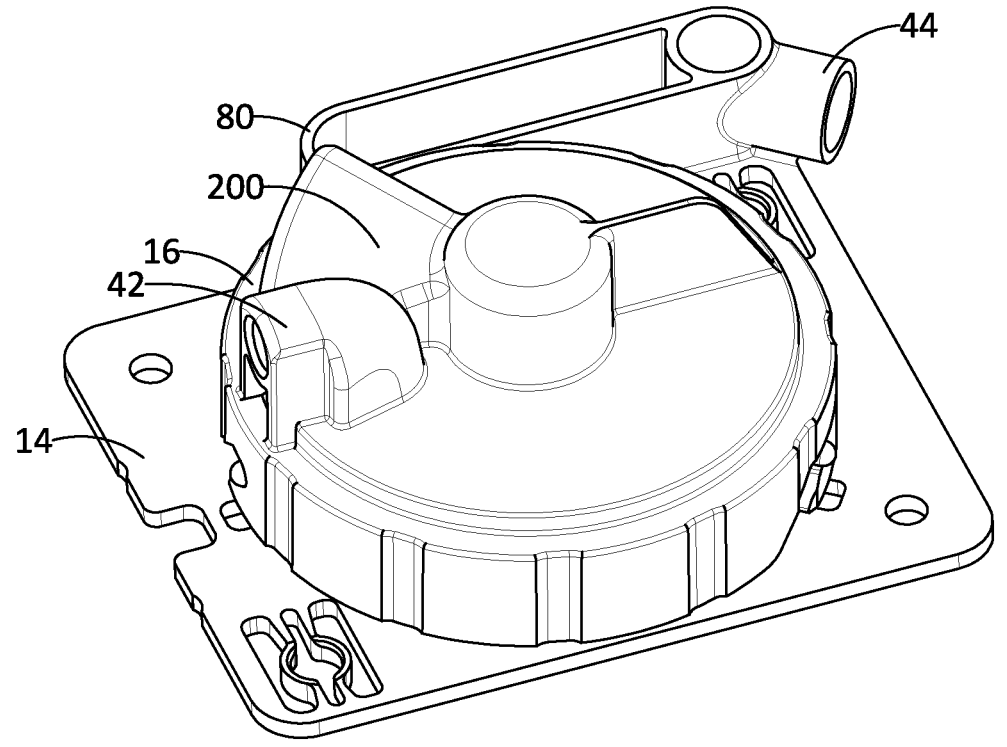
FIG. 14 illustrates another tissue holder assembly having a base, a cover and a tissue holder.

It should be noted that the tissue holder assembly 10 is not limited to the configuration shown in the above example, and that the tissue holder assembly 10 may have other configurations in other embodiments. For example, in other embodiments, the cover 16 of the tissue holder assembly 10 may have a slanted cover portion at least partially defining a vaulted compartment that is shielded from the inlet port (tissue entry port) 42. FIG. 14 illustrates another tissue holder assembly 10 in accordance with other embodiments. The tissue holder assembly 10 is the same as that described with reference to FIGS. 1-3, except that the cover 16 has a slanted cover portion 200. The slanted cover portion 200 at least partially defines a vaulted compartment that is shielded from the inlet port 42. The slanted cover portion 200 is advantageous because the slope allows for fluid run off. In other embodiments, the cover portion 200 may have other shapes. For example, in other embodiments, the cover portion 200 corresponding with the imaging space may have a dome shape, a pyramid shape, a trapezoidal shape, or other shapes.

Figure 15:
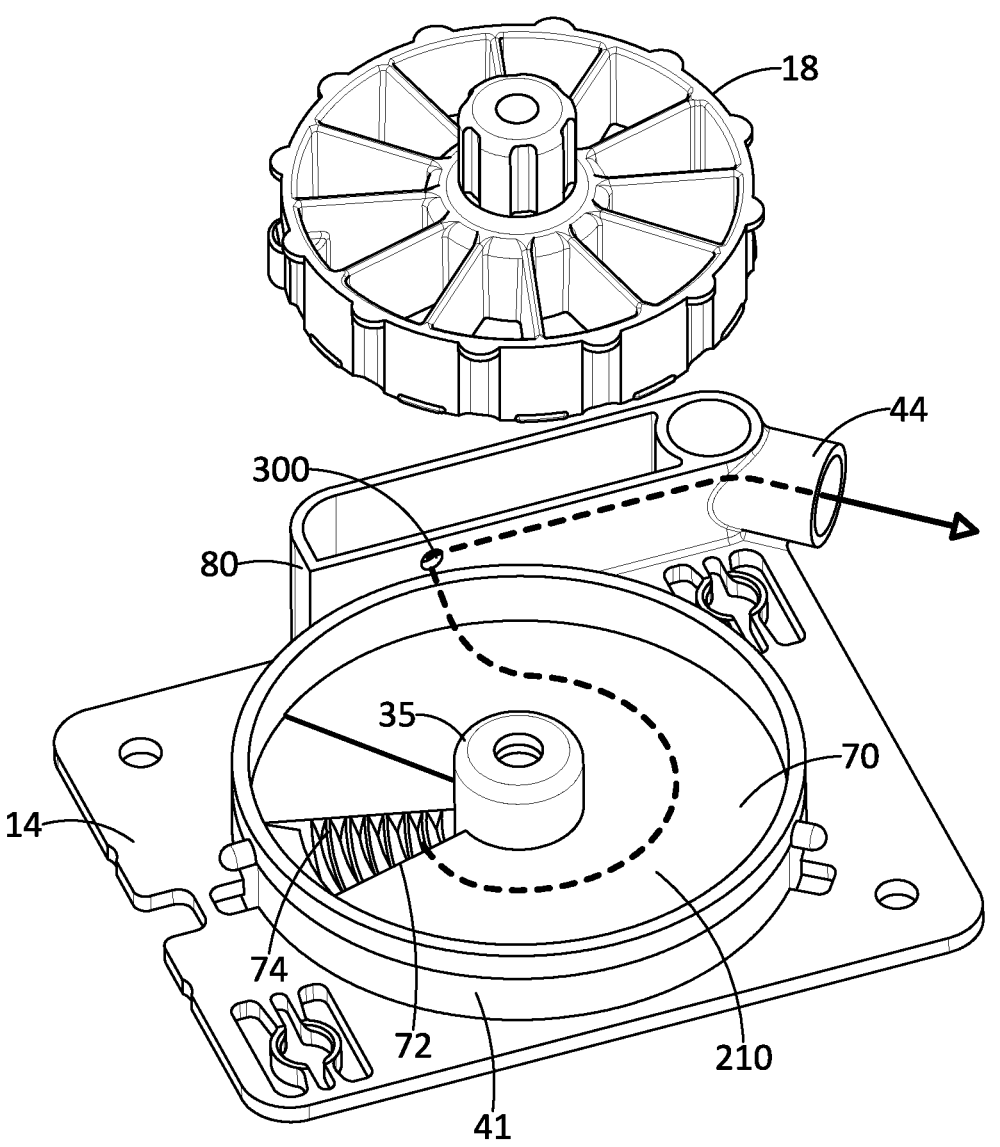
FIG. 15 illustrates the tissue holder assembly of FIG. 14, particularly showing the cover of the tissue holder assembly removed.

The tissue holder assembly 10 of FIG. 14 is also different from the one described with reference to FIGS. 1-3, in that the plenum 80 has a different size and shape. In particular, the plenum 80 of FIG. 14 has a volume that is larger than the one described previously. Also, the plenum 80 of FIG. 14 has a height that is taller than the circumferential sidewall 41 of the base 14 (see FIG. 15). FIG. 15 illustrates the tissue holder assembly 10 of FIG. 14, particularly showing the cover 16 of the tissue holder assembly 10 removed. As shown in the figure, the plenum 80 has an opening 300 for receiving fluid from the fluid channel 78 (not shown) under the platform 70. The opening 300 and the outlet port 44 are located at opposite ends of the plenum 80. During use, fluid from the bottom of the tissue holder 18 enters the platform opening 72, and is broken up by the flow comb 74 inside the fluid channel 78 (not shown) under the platform 70. As shown in FIG. 15, suction in the channel 78 causes the fluid to be transported along the channel 78 that extends circumferentially around the hub 35. The fluid then enters into the opening 300 at a wall of the plenum 80 to reach the cavity in the plenum 80. The fluid is then suctioned out of the plenum 80 via the outlet port 44.

The path of the fluid is represented by the dashed arrow 210 in the figure.

Figure 16:
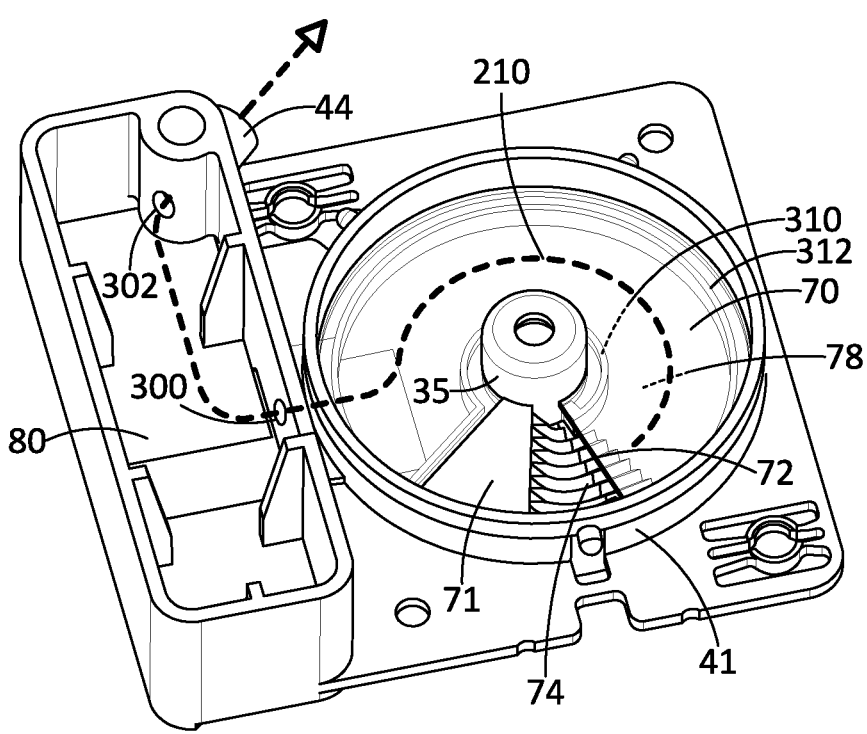
FIG. 16 illustrates a partial transparent view of a base of another tissue holder assembly.
Figure 17:
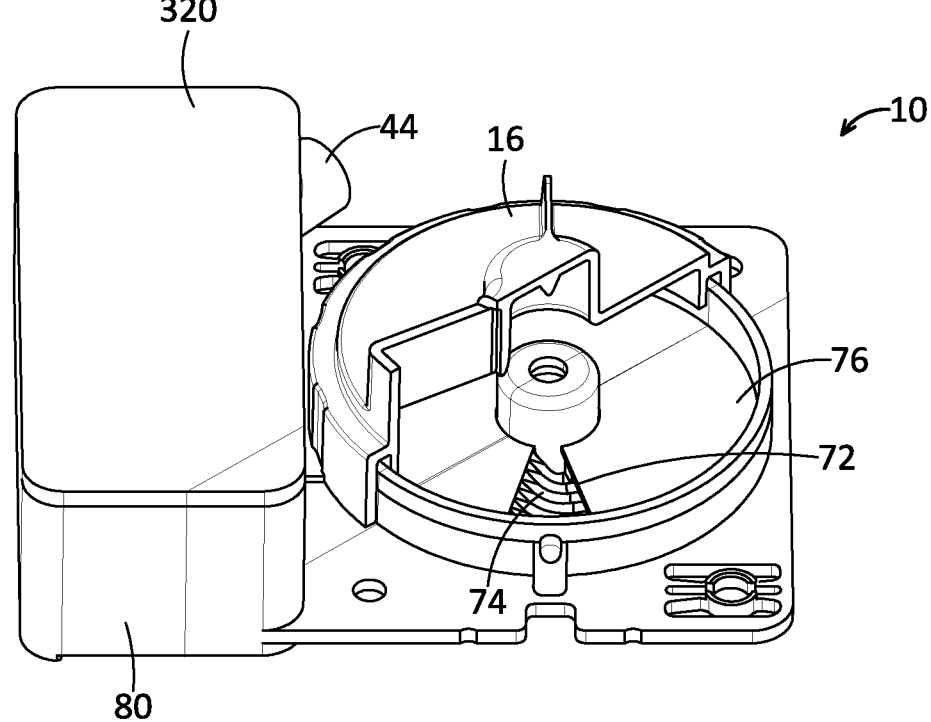
FIG. 17 illustrates the tissue holder assembly of FIG. 16, without the tissue holder, and with the cover partially shown.

FIGS. 16-17 illustrate another tissue holder assembly 10 in accordance with other embodiments. The tissue holder assembly 10 is the same as the one described with reference to FIGS. 1-3, except that the plenum 80 has a different size and shape. In particular, the plenum 80 of FIGS. 16-17 has a volume that is larger than the one described previously with reference to FIGS. 1-3. Also, the plenum 80 of FIG. 16 has a height that is taller than the circumferential sidewall 41 of the base 41. As shown in FIG. 16, the plenum 80 includes a wall with a first opening 300 that is in fluid communication with the fluid channel 78 under the platform 70. The plenum 80 also includes a second opening 302 that is in fluid communication with the outlet port 44. In FIG. 16, the platform 70 is illustrated in a partial transparent configuration to show the components underneath it. As shown in the figure, the tissue holder assembly 10 includes channel sidewalls 310, 312 that cooperate with the platform 70 and the bottom member 76 (shown in FIG. 17) to define the channel 78.

During use, fluid enters the platform opening 72, and is broken up by the flow comb 74 inside the fluid channel 78 under the platform 70. As shown in FIG. 16, suction in the channel 78 causes the fluid to be transported along the channel 78 that extends circumferentially around the hub 35. The fluid then enters into the first opening 300 at the wall of the plenum 80 to reach the cavity in the plenum 80. The fluid is then suctioned out of the second opening 302 at the plenum 80, and exits via the outlet port 44. The path of the fluid is represented by the dashed arrow 210 in the figure.

As shown in FIG. 17, the tissue holder assembly 10 also includes a plenum cover 320 for covering the plenum 80. The platform 70 and the channel sidewalls 310, 312 are removed to show the bottom member 76 of the base 14.

In other embodiments, the sidewalls 310, 312 are optional, and the exterior wall of the hub 35 and the interior surface of the circumferential sidewall 41 may define the width of the fluid channel 48.

The tissue holder assembly 10 may have other configurations in other embodiments, and should not be limited to the embodiments described. For example, in one or more embodiments described herein, the flow comb 74 is optional, and the tissue holder assembly 10 may not include the flow comb 74. Also, in other embodiments, the plenum 80 is optional, and the tissue holder assembly 10 may not include the plenum 80. In such cases, the suction line 48 may be coupled to the circumferential sidewall 41 of the base 14, and the circumferential sidewall 41 of the base 14 may include an opening for coupling with the suction line 48. In further embodiments, the plenum 80 may be located away from the base 14. For example, the suction line 48 may be connected to the plenum 80 that is away from the base 14, and another suction line coupled to the plenum 80 may apply suction to remove fluid inside the plenum 80.

FIG. 18 illustrates a method 1800 of removing fluid from a tissue holder. The method 1800 is performed using the tissue holder assembly 10. The method 1800 includes receiving, by the tissue holder, a tissue sample and fluid, wherein the tissue holder comprises a bottom with a filter, and wherein the tissue holder is rotatably coupled to a base of a tissue holder assembly, the base having a hub (item 1802). The method 180 also includes applying suction to remove the fluid from the bottom of the tissue holder, wherein the suction is applied through a fluid channel that is under a platform of the tissue holder assembly below the tissue holder (item 1804). The method 1800 further includes transporting the removed fluid via the fluid channel, wherein the removed fluid is transported by the fluid channel around the hub of the base in a unidirectional manner (item 1806).

Optionally, in the method 1800, the removed fluid is transported to a plenum. Optionally, the method 1800 further includes breaking up the fluid via a flow comb. Optionally, the method 1800 further includes a platform opening, and wherein the flow comb is below the platform opening and extends within the fluid channel. Optionally, in the method 1800, the tissue holder assembly comprises a base having a base member, the base member and the platform defining the fluid channel, and wherein the fluid is transported between the base member and the platform. Optionally, in the method 1800, the removed fluid is transported along an arc path. Optionally, the method 1800 further includes a platform opening, wherein the tissue holder assembly comprises a cover with a tissue entry port, and wherein the method further comprises delivering the tissue sample via the tissue entry port onto the tissue holder at a location that is above the platform opening.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A tissue holder assembly comprising:
a base, the base comprising a bottom member, a central hub extending upwardly from the bottom member along an axis, and a circumferential sidewall extending upwardly from the bottom member radially spaced apart from the hub, the circumferential sidewall surrounding the hub and defining an interior region configured for accommodating a cylindrical tissue holder;
the base further comprising a raised platform spaced upwardly apart from the bottom member, an upper portion of the central hub extending through a central opening of the platform, wherein the hub is configured for supporting the tissue holder, wherein the platform at least partially defines a platform opening extending circumferentially around the axis, the platform opening further defined by the hub on a radially inner side and the circumferential sidewall on a radially outer side;
the bottom member, the hub and the circumferential sidewall collectively defining an annular fluid channel underlying the platform, the fluid channel being in fluid communication with the platform opening;
wherein the fluid channel extends around the hub from the platform opening to a fluid exit port in the circumferential sidewall, to thereby provide unidirectional fluid flow around the hub of the base.

2. The tissue holder assembly of claim 1, further comprising a flow comb below the platform opening, the flow comb extending inside the fluid channel.

3. The tissue holder assembly of claim 2, wherein the flow comb has an arcuate shape.

4. The tissue holder assembly of claim 2, wherein the flow comb has a length that is longer than a dimension of the platform opening measured along a longitudinal axis of the fluid channel.

5. The tissue holder assembly of claim 1, further comprising a plenum, wherein the fluid channel is in fluid communication with the plenum.

6. A method of removing fluid from a tissue holder, the method comprising:
receiving, by the tissue holder, a tissue sample and fluid, wherein the tissue holder comprises a bottom with a filter, and wherein the tissue holder is rotatably coupled to a base of a tissue holder assembly, the base having a bottom member, a hub extending upwardly from the bottom member along an axis, and a circumferential sidewall extending upwardly from the bottom member radially spaced apart from the hub, the circumferential sidewall surrounding the hub and defining an interior region that accommodates the tissue holder, the base further including a raised platform spaced upwardly apart from the bottom member, an upper portion of the central hub extending through a central opening of the platform and supporting the tissue holder, the platform at least partially defining a platform opening extending circumferentially around the axis, the platform opening further defined by the hub on a radially inner side and the circumferential sidewall on a radially outer side;
applying suction to remove the fluid from the bottom of the tissue holder via the platform opening, wherein the suction is applied through a fluid channel that is under the platform of the tissue holder assembly below the tissue holder and defined by the bottom member, the hub, and the circumferential sidewall; and
transporting the removed fluid via the fluid channel, wherein the removed fluid is transported by the fluid channel around the hub of the base in a unidirectional manner.

7. The method of claim 6, wherein the removed fluid is transported to a plenum.

8. The method of claim 6, further comprising breaking up the fluid via a flow comb.

9. The method of claim 8, the flow comb is below the platform opening and extends within the fluid channel.

10. The method of claim 6, wherein the fluid is transported between the bottom member and the platform.

11. The method of claim 6, wherein the removed fluid is transported along an arc path.

12. The method of claim 6, the tissue holder assembly comprising a cover with a tissue entry port, wherein the method further comprises delivering the tissue sample via the tissue entry port onto the tissue holder at a location that is above the platform opening.

13. The tissue holder assembly of claim 2, wherein the flow comb comprises a plurality of flow channels.

14. The tissue holder assembly of claim 2, wherein the flow comb comprises a hydrophobic coating.

15. The tissue holder assembly of claim 2, wherein the flow comb comprises an anti-coagulant coating.

16. The tissue holder assembly of claim 5, wherein the plenum has a height that is greater than a height of the circumferential sidewall of the base.

17. The tissue holder assembly of claim 1, wherein the fluid channel is configured to provide the unidirectional fluid flow around the hub through an angular range that is at least 30°.

18. The tissue holder assembly of claim 17, wherein the fluid channel is configured to provide the unidirectional fluid flow around the hub through an angular range that is 300°.

19. The tissue holder assembly of claim 1, wherein the hub of the base comprises a spindle configured to receive the tissue holder, and wherein the platform extends circumferentially around at least a majority of a space between the hub and the circumferential sidewall.

* * * * *